(12) United States Patent
Turner

(10) Patent No.: US 6,706,947 B2
(45) Date of Patent: Mar. 16, 2004

(54) METHOD FOR SCREENING FOR AGENTS AGAINST CANCER USING AN IMMUNOSUPPRESSION ANIMAL MODEL

(75) Inventor: John Harvey Turner, Dalkeith (AU)

(73) Assignee: Fremantle Hospital, Fremantle (AU)

( * ) Notice: Subject to any disclaimer, the term of this patent is extended or adjusted under 35 U.S.C. 154(b) by 0 days.

(21) Appl. No.: 10/262,089

(22) Filed: Sep. 30, 2002

(65) Prior Publication Data

US 2003/0101466 A1 May 29, 2003

Related U.S. Application Data

(62) Division of application No. 09/155,237, filed as application No. PCT/AU97/00185 on Mar. 21, 1997, now Pat. No. 6,538,174.

(30) Foreign Application Priority Data

Mar. 21, 1996 (AU) .............................................. PN 8803

(51) Int. Cl.$^7$ ....................... A01K 67/00; A01K 67/027; A01N 63/00; A61K 48/00
(52) U.S. Cl. ................. 800/9; 800/8; 800/10; 800/14; 800/15; 800/16; 800/17; 424/93.1; 424/93.2; 424/93.7; 424/9.1
(58) Field of Search ............................ 800/8, 9, 10, 14, 800/15; 424/93.2, 93.1, 93.7, 9.1; 514/44; 435/320.1, 325, 455

*Primary Examiner*—Jeffrey Fredman
*Assistant Examiner*—Sumesh Kaushal
(74) *Attorney, Agent, or Firm*—Fulbright & Jaworski L.L.P.

(57) ABSTRACT

The invention relates to an animal model of cancer. The animal carries a tumour xenograft and is immunosuppressed by administration of cyclosporin and ketoconazole. The model is useful for studying cancer and treatment thereof.

11 Claims, 29 Drawing Sheets

Area under blood concentration − time curve (ng/ml.h)

B16M

HT-29

HT-29

METHOD FOR SCREENING FOR AGENTS AGAINST CANCER USING AN IMMUNOSUPPRESSION ANIMAL MODEL

RELATED APPLICATIONS

This application is a divisional of Ser. No. 09/155,237, filed Sep. 21, 1998 now U.S. Pat. No. 6,538,174, which is a 35 U.S.C. §371 filing of PCT/AU97/00185, international filing date Mar. 21, 1997, which claims priority of Australian Application DN8803, filed Mar. 21, 1996.

This invention relates to a large animal model of human cancer, in particular in ruminant animals such as sheep which are immunosuppressed by cyclosporin A and ketoconazole and which carry transplanted human or murine tumours, or both. The invention also relates to the use of such an animal model in the study of cancer, particularly for evaluating candidates for radio-, chemo- or radiopharmaceutical therapy or radio-immunotherapy. The animal model is also useful for radio-imaging of neoplasms or tumours, and for the study of metastasis.

BACKGROUND OF THE INVENTION

At present there is no effective method available for treatment of many solid tumours such as malignant melanoma or cancer of the colon, breast or ovary once the primary tumour has metastasised. Radiolabelled monoclonal antibodies against tumour-associated antigens offer a unique potential for targeting radiotherapy to disseminated tumour cells which may ultimately lead to effective treatment of metastatic cancer. Radioimmunotherapy has been shown to be effective in haematological malignancy, but problems of tumour localisation and penetration have so far prevented successful treatment of solid tumour metastasis.

In order to evaluate therapeutic agents, or methods of imaging tumours, and to study the biological processes taking place in the development and metastasis of solid tumours, it is essential to use animal models of cancer. The biodistribution of radiolabelled monoclonal antibodies can only be determined in the intact animal, where the influences of serum protein binding, vascular permeability, interstitial pressure and enzymatic breakdown all affect therapeutic radiation of the target tumour and determine the background irradiation of normal tissues. This essential dosimetry cannot be performed in vitro.

The immune-incompetent nude mouse, and less commonly, the nude rat, are the only models which are widely used for in vivo study of human tumours. The tumours are usually transplanted subcutaneously in these rodents. The major problem associated with human tumour xenografts in nude animals is the disproportionate size of the tumour in relation to the total body weight of the animals, which precludes accurate, predictive pharmacokinetic studies of potential chemotherapeutic and radiopharmaceutical treatments for human cancer, and adversely affects the usefulness of such models for imaging studies.

Similar problems are encountered in orthotopic implantation models, in which human tumours or tumour cells are transplanted or injected into the organ or tissue of origin in recipient immunodeficient athymic mice (Manzotti et al, 1993). Although metastasis of the transplanted tumour is achieved, accurate and reliable data on usefulness of therapeutic agents or methods are still limited by the disproportionate size of the tumour in relation to the total body weight of the mouse.

Therefore, a large animal model would be more suitable as a model of cancer and for detailed study of targeted cancer therapy. Large animal models of human cancer are not readily available, because of the difficulty of establishing tumours in such hosts; the xenografts usually do not grow or are rejected.

An animal model which would allow investigation of tumour nodules of a specific size and location, and which would simulate patterns of metastasis in various types of cancer, is particularly desirable. Larger animal models will also permit more effective and accurate evaluation of potential methods of therapy and imaging, and better characterisation of the biological events taking place during development and treatment of such cancers.

One way of inducing acceptance of xenografts is the administration of Cyclosporin A (CSA), a cyclic fungal peptide produced by *Tolypocladium inflatum* Gams. CsA is a neutral cycloundecapeptide with potent immunosuppressive properties (Borel, 1989; Di Padova, 1989; Hess et al, 1988). This antifungal metabolite appears to inhibit both humoral and cellular immune responses by selectively interfering with T-cell activation (Borel, 1989; Di Padova, 1989; Hess et al, 1988). CsA has been shown to be effective in preventing transplant rejection in both humans and animals, but its use is often limited by its toxic side-effects (Borel, 1989; Reynolds et al, 1992; Russ, 1992), and by the high concentrations required in order to induce immunosuppression. The normal vehicle used, Cremaphor EL, can also induce severe toxic side effects.

For example, rabbits given intramuscular injections of CsA at 10 mg/kg suffered from toxic side effects, and became anorexic and developed pneumonia. These effects were only eliminated if larger animals were used, and antibiotic and fluid therapy were instituted together with cyclosporin administration (Ligget et al, 1993). Cats also require high oral doses of CsA in order to accept human tumour xenografts, since intravenous administration is also associated with species-specific Cremaphor-induced vasoconstriction with histamine release and anaphylaxis (Bowers et al, 1991).

However, in sheep, infusion of the castor-oil based vehicle for CsA, Cremaphor EL, is well tolerated (Tresham et al, 1988). There is also no nephrotoxic reaction to intravenous CsA in sheep (Tresham et al, 1990). A recent pharmacokinetic study of CsA administered intravenously to sheep revealed data similar to that reported in human transplant patients (Charles et al, in press), and no toxic effects were described.

In addition to the toxic effects of CsA, a major disadvantage of this compound is the requirement for daily injections, which is both tedious and expensive and limits the period of time within which animals can be kept for observations (Hu et al, 1994, and de Ward-Siebinga et al, 1994). In all the studies mentioned above, the amount of CsA administered has been more than 10 mg/kg of animal weight.

There has been a single brief report of experiments in which human melanoma tumours have been subcutaneously grown in dogs immune-suppressed by oral CsA (Wiseman et al, 1991). This method, however, also requires high doses of CsA due to its limited bioavailability from oral administration. The intravenous route is precluded by the anaphylactic reaction of dogs to the Cremaphor vehicle in which cyclosporin is dissolved (Bowers et al, 1991).

More recently, several groups have reported the use of ketoconazole in conjunction with CsA as a means of reducing the dose of CsA required in transplant patients to maintain immunosuppression and prevent graft rejection (Gandhi et al, 1992; Butman et al, 1991; First et al, 1991;

Wadhwa et al, 1987). Ketoconazole is a synthetic imidazole dioxolane used primarily for the treatment of superficial fungal infections, chronic mucocutaneous candidiasis and genital candidiasis (Bodey, 1992; Breckenridge, 1992; Borelli et al, 1979). Ketoconazole indirectly enhances the bioavailability of CsA by inhibiting the hepatic cytochrome P-450 mixed function oxidase system which is primarily responsible for CsA inactivation in vivo (Breckenridge, 1992; First et al, 1991; Wadhwa et al, 1987). Increased bioavailability reduces the dose of CsA required for therapeutic efficacy, which, in turn, decreases the toxicity associated with its use.

Ketoconazole, in addition to its synergism with CsA in the induction and maintenance of immunosuppression, has been reported to exert anti-tumour activity against certain types of cancer (Eichenberger et al, 1989a; Mahler and Denis, 1992). Ketoconazole also acts in synergy with anti-neoplastic drugs (vinblastine, etoposide) to inhibit the growth of human prostate carcinoma cells in vitro (Eichenberger et al, 1989b).

Similarly, CsA has been shown to inhibit cell division of both normal and malignant cells in vivo and in vitro (Borel, 1989; Di Padova, 1989; Barbera-Guillem et al, 1988; Kreis and Soricelli, 1979). Of the cell lines tested, human and murine T cell lymphomas and leukaemias were found to be sensitive to CsA-induced growth inhibition at doses of 0.5–5 µg/ml, whereas non-lymphoid cell lines and certain murine B and null cell leukaemias were insensitive to doses of up to 10 µg/ml (Borel, 1989).

We have surprisingly found that concomitant oral administration of ketoconazole and CsA to a mammal produces immunosuppression which allows xenografting of cancer cells or tissues and provides a large animal model for the study of cancer. This is particularly unexpected, in view of the anti-tumour effects of ketoconazole and CsA, and the difficulty of inducing and maintaining immunosuppression with non-toxic doses of CsA.

A main advantage of the animal model according to the present invention is the cost effectiveness of obtaining and maintaining the animals. No aseptic or sterile conditions are necessary and the animals can be maintained on a normal diet.

Our model also permits investigation of tumour nodules of desired size at predetermined sites, which simulate the usual patterns of metastasis of particular cancers.

SUMMARY OF THE INVENTION

Thus, in one aspect the invention provides an animal model of cancer, comprising a mammal which is immunosuppressed by administration of cyclosporin and ketoconazole, and which carries a tumour xenograft.

Preferably, the mammal is selected from the group consisting of sheep, goats, cattle, pigs or the like. More preferably, the mammal is a sheep. In a particularly preferred embodiment, the mammal has a plurality of xenografted tumours implanted subcutaneously.

Tumour cell lines which may be used in this model include but are not limited to cells from solid tumours, such as those present in cancer of the colon, breast or ovary, or melanoma. Cell lines or spheroids derived from cancerous cells are particularly useful for the purposes of the invention, for example LS174T, HT-29 and colon cancer and SKMEL melanoma cell lines. The tumour may be of human or non-human origin, but is preferably of human or murine origin.

It is particularly preferred that the tumours are introduced into the model of the invention using orthotopic transplantation.

In a particularly preferred embodiment of the invention, tumour cells or tumours are transplanted into the host animal using Matrigel as the vehicle. Matrigel is a reconstituted basement-—membrane preparation which facilitates tumour uptake at sites of incubation.

In a second aspect, the invention provides a method of evaluating the efficacy of a putative therapeutic agent against cancer, comprising the step of administering said agent to a ruminant mammal model of the invention.

The agents which may be tested in this model include but are not limited to immunochemotherapeutic agents, cytokines, chemotherapeutic agents and radiopharmaceuticals, and may also comprise internal or external radioactive agents as well as radiolabelled peptides. Gene therapy may also be evaluated using this model.

In a third aspect, the invention provides a method of evaluating the efficacy of a method of radioimaging of tumours or neoplasms, comprising the stepof administering a radiolabelled, tumour-specific antibody to the ruminant mammal model of the invention.

The radiolabelled antibody may be a monoclonal or polyclonal antibody comprising a radiolabel, preferably selected from the group consisting of Technetium-99m, Indium-111, Iodine-131, Rhenium-186, Rhenium-188, Samarium-153, Lutetium-177, Copper-64, Scandium-47, Yttrium-90. Monoclonal antibodies labelled with therapeutic radionuclides such as Iodine-131, Rhenium-188, Holmium-166, Samarium-153 and Scandium-47, which do not compromise the immunoreactivity of antibodies and are not broken down in viva, are especially preferred. The person skilled in the art will appreciate that other radioactive isotopes are known, and may be suitable for specific applications. Similarly it will be clearly understood that the term "antibody" encompasses fragments and analogues such as Fab, Fv and ScFv, provided that the binding activity is retained. Peptide fragments of antibodies are specifically contemplated by the invention. The fragments or analogues may be prepared using recombinant DNA methods or by synthetic methods such as solid-phase synthesis. The radioimaging may be conducted using Single Photon Emission Computer Tomography (SPECT), Position Emmission Tomography (PET), Computer Tomography (CT) or Magnetic Resonance Imaging (MRI). Correlative imaging, which permits greater anatomical definition of location of metastases located by radioimmunoimaging, is also contemplated.

In a fourth aspect, the invention provides a method of screening of therapeutic radiolabelled peptides directed against tumours, preferably tumour-associated receptors, antigens or ligands or the like. Therapeutic radiolabelled peptides such as 90 Yttrium-labelled octreotide or $^{111}$Indium-labelled octreotide are contemplated. Radiolabelled antibodies to tumour-associated ligands or antigens and therapeutic agents linked to such entities are also within the scope of the invention.

In a fifth aspect, the invention provides a method of producing a ruminant mammal bearing a tumour xenograft, comprising the step of concomitant administration of CsA and ketoconazole to the mammal. Preferably the ketoconazole is administered in a drench formulation which by-passes the rumen and is absorbed in the abomasum. This provides highly reproducible bioavalability and predictable competitive inhibition of CsA metabolism in the liver.

Preferably, the dose of CsA is in the range 2.5 to 3.5 mg per kg administered twice a day and the dose of ketoconazole is 5 to 10 mg per kg administered twice a day. In a particularly preferred embodiment, 10 mg/kg ketoconazole is administered twice a day to maintain trough serum levels of CsA within the range 1000–1500 ng/ml.

The model system of the invention enables the testing of therapeutic methods directed against primary malignancy or metastatic cancer in a manner which has hitherto not been possible. The model is suitable for testing of radiotherapy, immunotherapy (including the use of cytokines), chemotherapy, and gene therapy. The model is also useful for testing of targeting or localisation agents, methods of imaging, and methods for monitoring the progress of therapy.

In a sixth aspect, the invention provides a method of direct transplantation of a xenogeneic tumour, comprising the step of transplanting a surgically-removed specimen into a mammal which is immunosuppressed by administration of cyclosporin and ketoconazole and allowing the specimen to metastasize in said mammal.

In a seventh aspect, the invention provides a method-of stimulating spontaneous metastasis of tumour cells to a target site such as the liver or lymph nodes, comprising the step of transplanting said cells to a mammal which is immunosuppressed by administration of cyclosporin and ketoconazole and allowing the cells to metatasize in said mammal.

In a eighth aspect, the invention provides a composition comprising a CsA or cyclosporin-like compounds and ketoconazole or related compounds, together with a pharmaceutically acceptable carrier.

In a ninth aspect, the invention provides a kit comprising a CsA or cyclosporin-like compound and ketoconazole or a related compound, wherein the ketoconazole or related compound increases the bioavailability of the CsA or cyclosporin-like compound and enhances the establishment of tumour xenografts.

It will be clearly understood that, although the invention has been described in detail with reference to immunosuppression using CsA whose bioavailability is enhanced with ketoconazole, the invention also contemplates the use of immunosuppressive compounds related to CsA, such as those disclosed in U.S. Pat. No. 4,117,118, synthetic or natural analogues of CsA such as CsB to I, or the compounds disclosed in Australian Patent No. 660623 by Vertex Pharmaceuticals, Inc.

In addition, there are other compounds which the person skilled in the art will recognise as being suitable to improve bioavailability of CsA, such as compounds related to ketoconazole (including, but not limited to, fluconazole), and calcium channel blockers.

Without wishing to be bound by any proposed mechanism for the observed advantages, it is believed that ketoconazole, which bears no chemical structural relationship to CsA, competes with hepatic enzymes which break down CsA.

DETAILED DESCRIPTION OF THE INVENTION

The invention will now be described by way of reference only to the following non-limiting examples, and to the figures, in which.

Figure 3B:
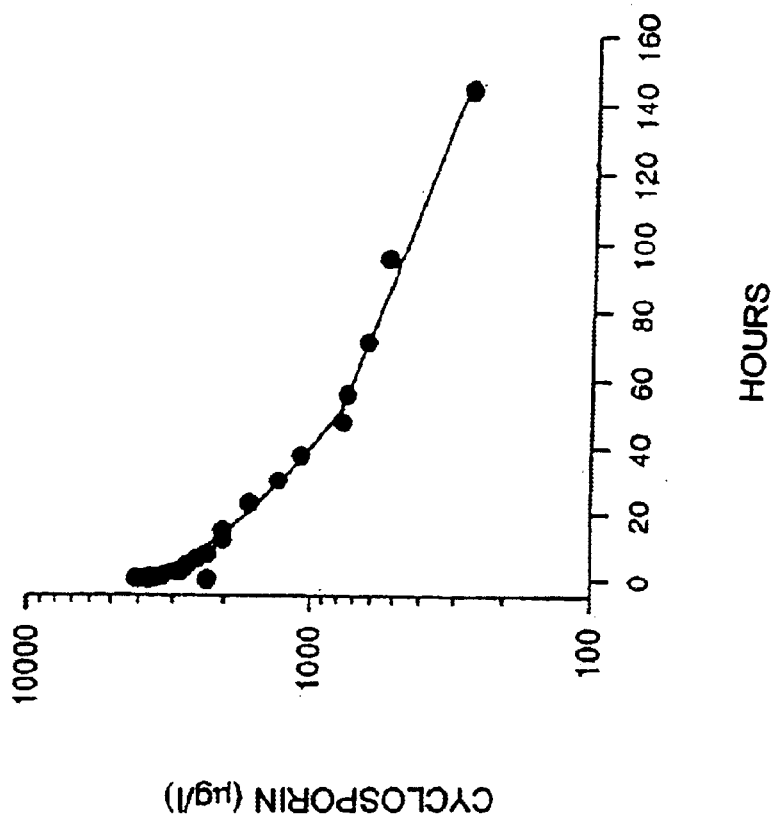
Figure 3A:
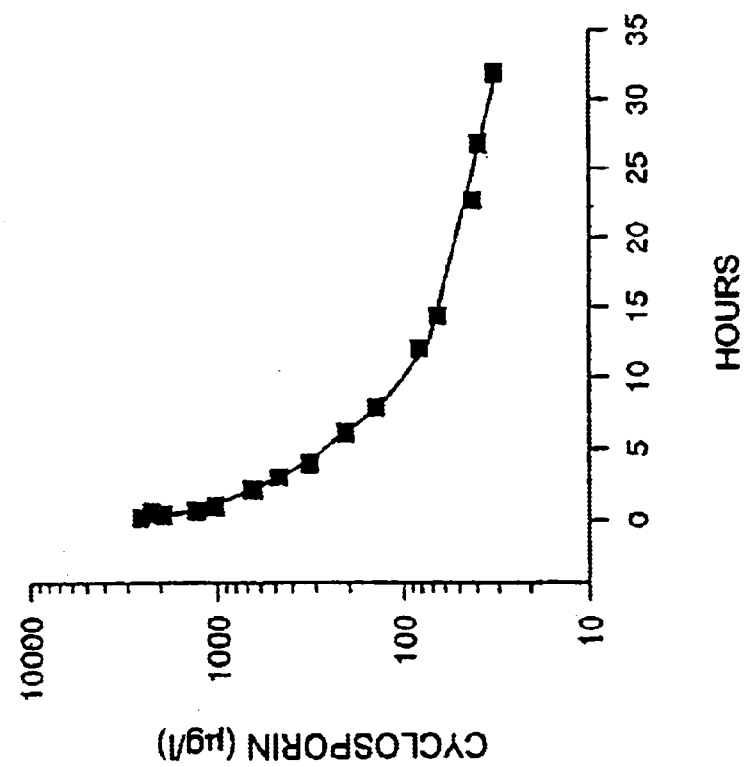

FIG. 3 shows the pharmacokinetic concentration-time profiles for CsA (3 mg/kg intravenously (iv) in sheep #14 in Example 1, after the first dose ■; day 0) and at steady-state (●; day 18) in the presence of ketoconazole (10 mg/kg orally (po). The solid lines show the log-linear regression fitted line for the last 5 data points.

Figure 4:
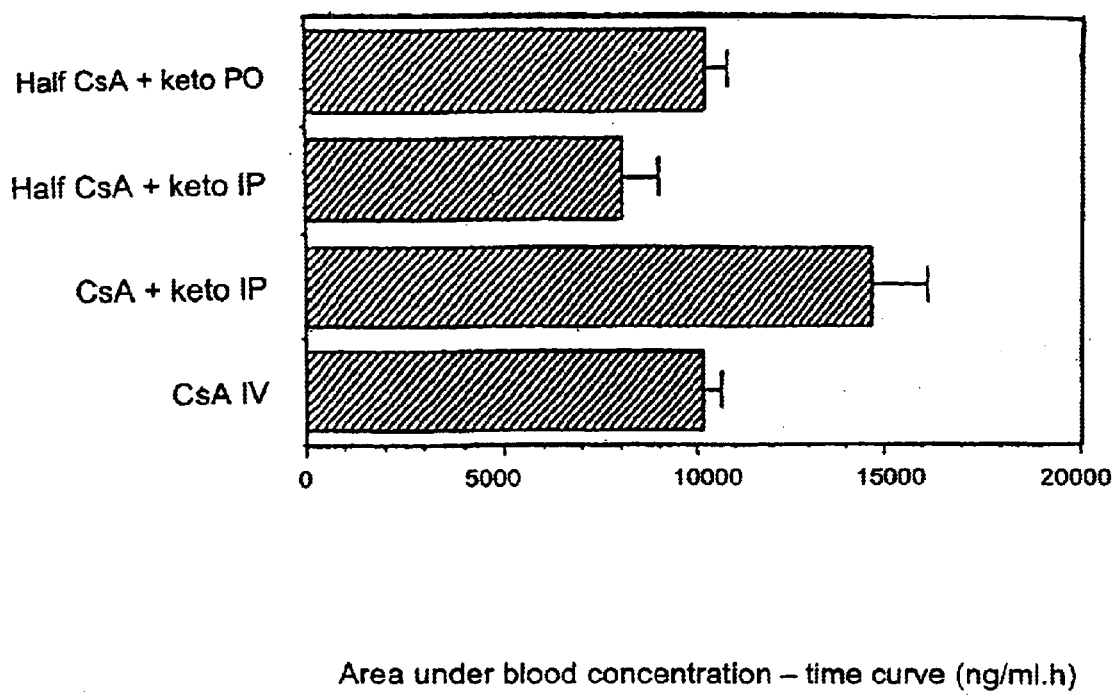

FIG. 4 is the area under the blood concentration—time curve, AUC, over 24 hours following CsA administration. The dose of ketoconazole was 10 mg/kg. The full dose of CsA was 5 mg/kg and the half dose was 2.5 mg/kg. Asterisks indicate significantly different AUC values relative to a full dose of CsA alone administered iv ($p<0.05$, Dunnett's test).

FIGS. 5($a$), ($b$) and ($c$) show the mitogen-stimulated lymphocyte proliferation responses after CsA (5 mg/kg iv) administration. Individual and mean responses of 5 individuals to ConA (a), PHA (b) and PWM (c) administration are shown as a percentage of the mean change in counts per minute ($\Delta$ cpm) of 5 sheep. Interassay coefficients of variation (based on background cpm data from individual sheep assayed on 6 different days) were between 75.7–126.6%.

FIGS. 5($d$), ($e$) and ($f$) show the mitogen-stimulated lymphocyte proliferation responses after CsA (5 mg/kg iv) administration in combination with ketoconazole (10 mg/kg). Individual and mean responses of 6 individuals to ConA (d), PHA (e) and PWM (f) are shown as a percentage of the mean day 0 delta cpm of 6 sheep. Interassay coefficients of variation (based on background cpm data from individual sheep assayed on 6 different days) were between 39–161%.

Figure 6:
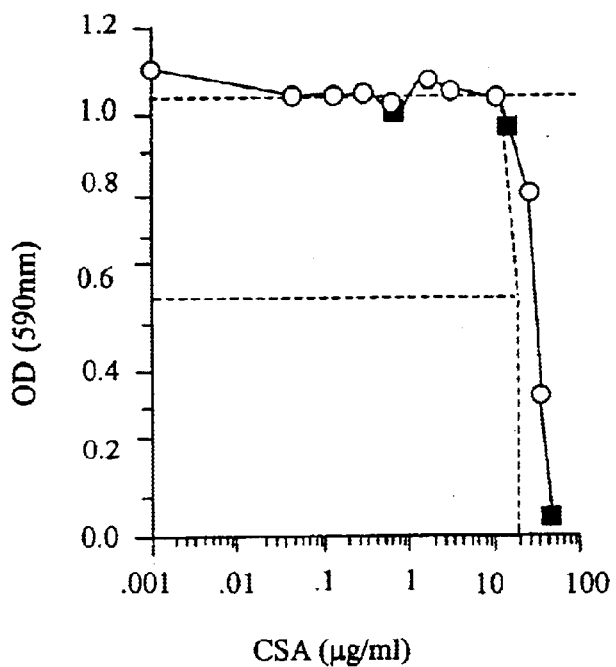
Figure 6:
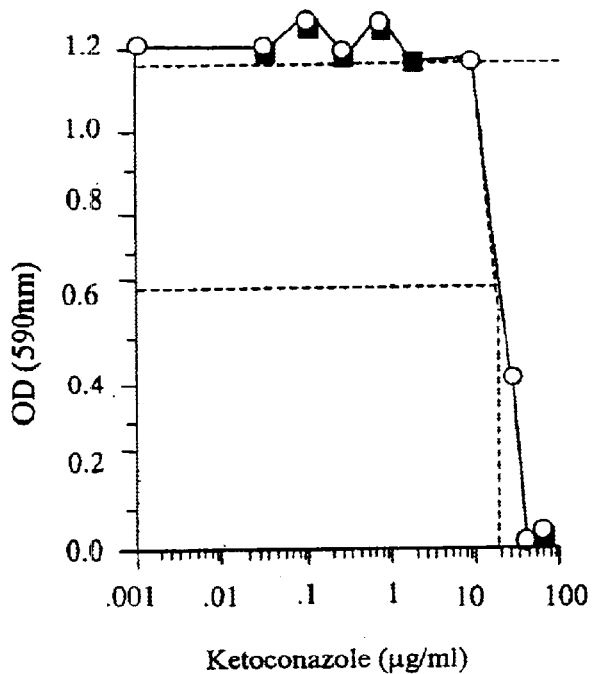
Figure 6:
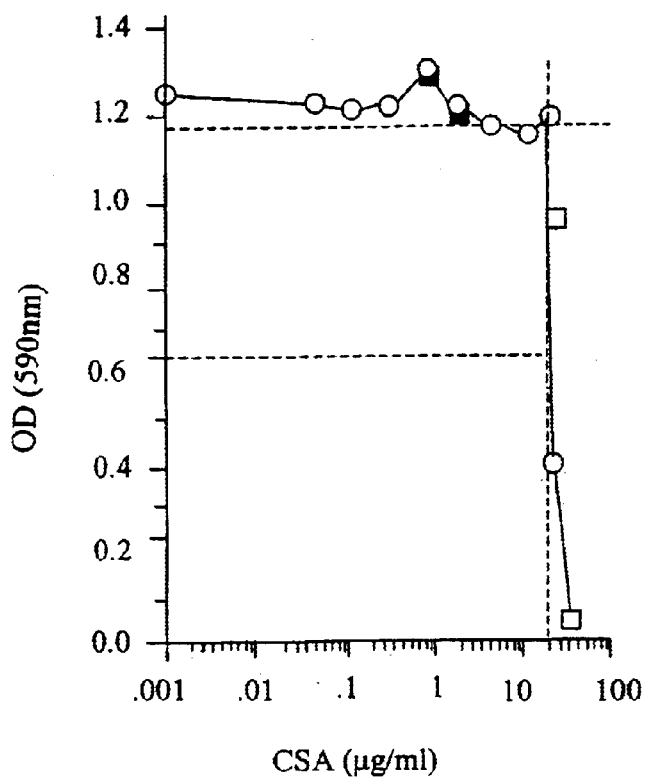
Figure 6:
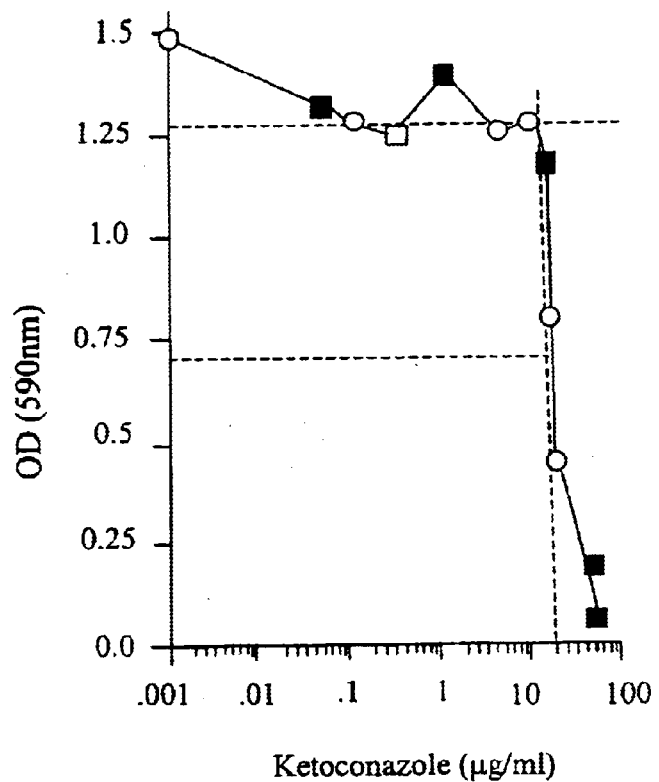
Figure 6:
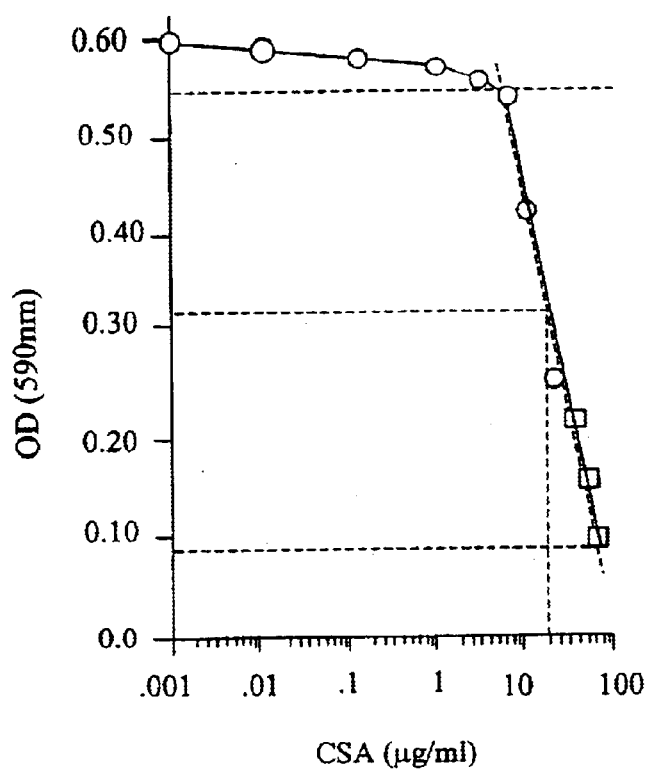
Figure 6:
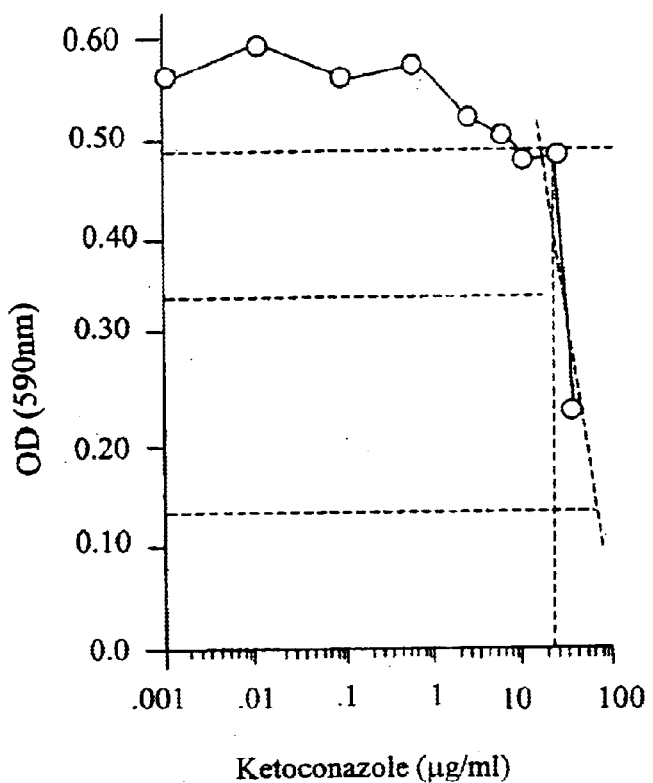

FIG. 6 shows the $ED_{50}$ of CsA and ketoconazole in three tumour cell lines—B16M, HT-29 and SKMEL, represented as tumour cell growth (OD 590 nm) in the presence of increasing concentrations of CsA (0–60 $\mu$g/ml) and ketoconazole (0–60 $\mu$g/ml) (log scale). A representative CsA and ketoconazole growth inhibition curve is shown for each cell line.

Figure 7:
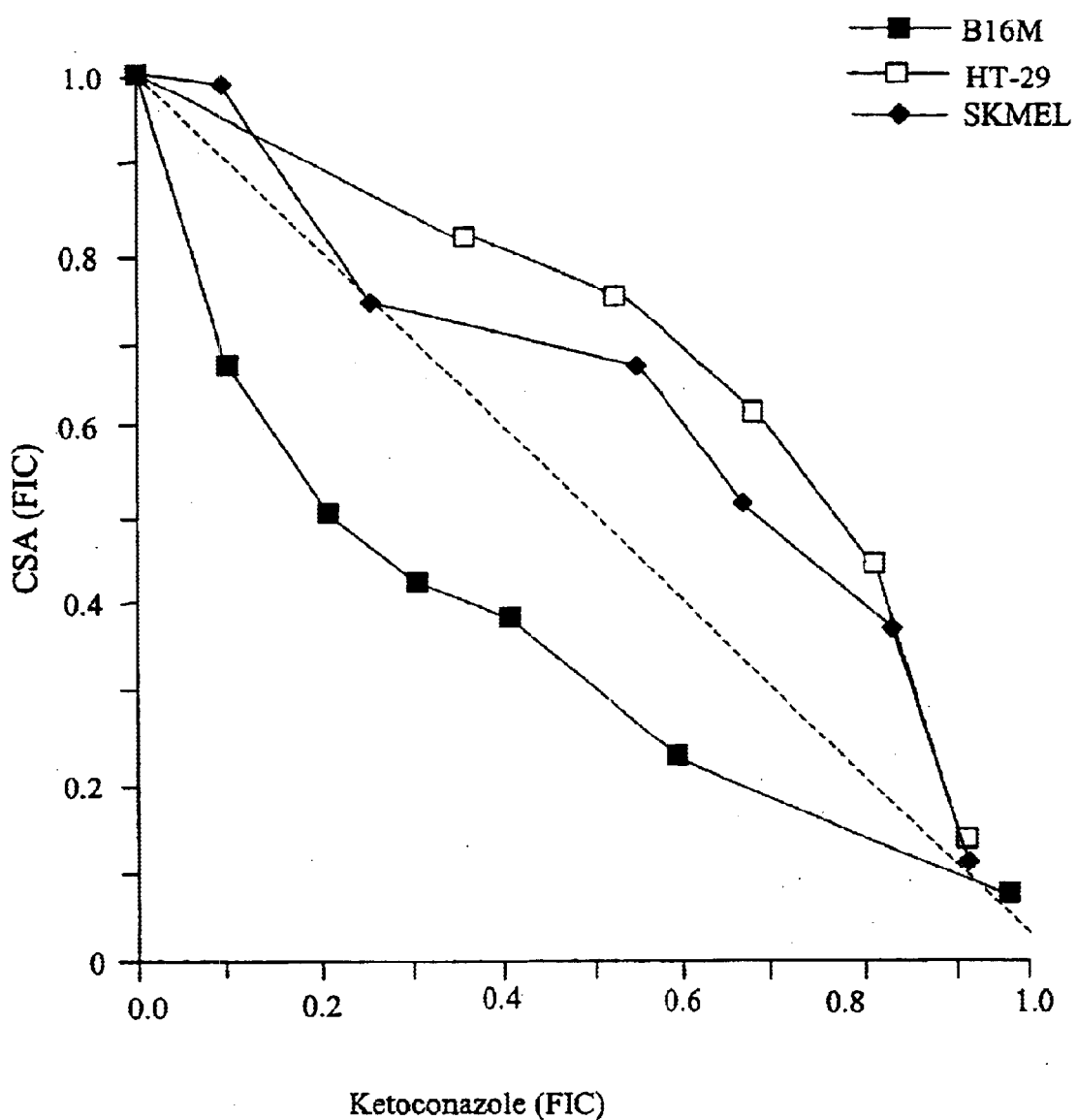

FIG. 7 shows the isobologram analysis of the effects of combination CsA/ketoconazole on tumour cell growth in vitro. The $ED_{50}$s of CsA in the presence of 3 sub-optimal concentrations of ketoconazole (no circle) and ketoconazole in the presence of 3 sub-optimal concentrations of CsA (circled) are presented as the FIC for each reagent. A representative isobologram is given for each cell line. The dotted line depicts the expected shape of the curve if the interaction is additive and is given for comparison.

Figure 8A:
Figure 8B:
Figure 8C:
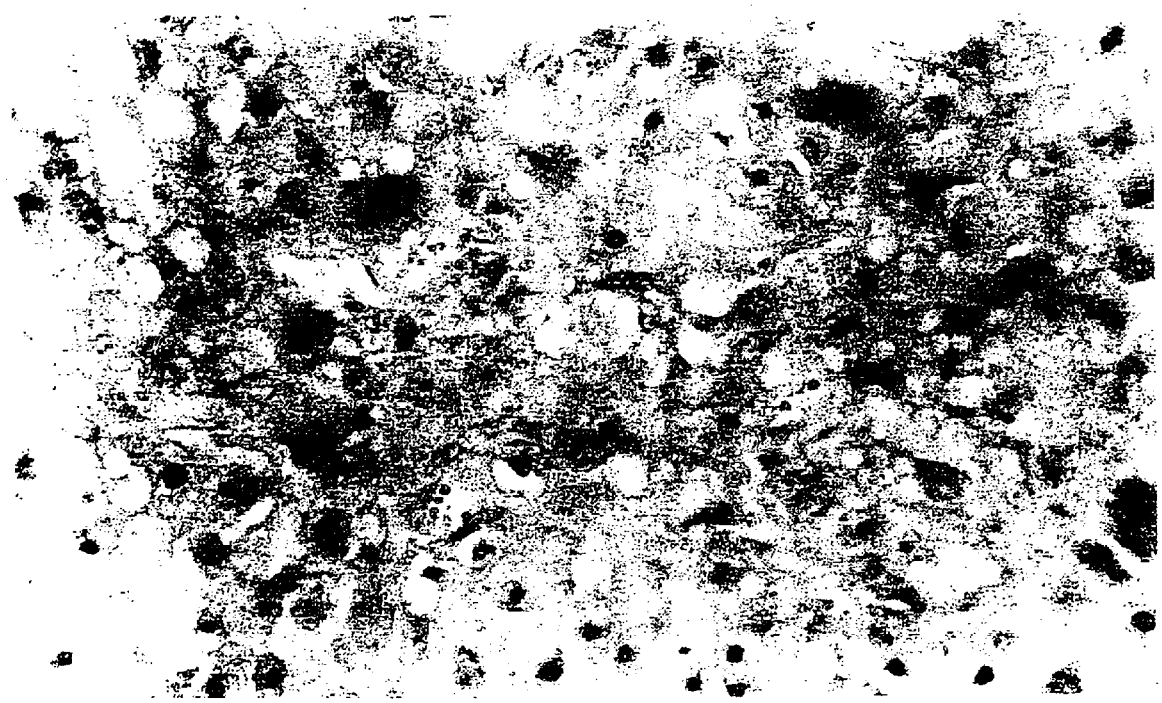

FIGS. 8–15 show the effects of transplantation of various cell lines into sheep immunosuppressed with cyclosporin and ketoconazole. Cells were inoculated as suspensions or spheroids with or without Matrigel, and tumour xenografts were examined macroscopically and fixed in formalin:

FIG. 8 is a photograph of SK-melanoma tumour deposit in skin.

Panel A shows diffuse sheets of malignant cells of "epithelioid" type with abundant amphophilic cytoplasm, vesicular nuclei and variably prominent nucleoli. Moderate nuclear pleomorphism is seen and mitotic figures are easily found. There is no evidence of necrosis and a minor chronic inflammatory cellular exudate is present at the periphery with no significant numbers of tumour infiltrating lymphocytes (H&E stain).

Panel B shows a positive granular cytoplasmic staining together with some nuclear staining with the immunoperoxidase preparation S100.

Panel C is a Mason Fontana preparation which shows no definite pigment deposition.

Figure 9A:
Figure 9B:
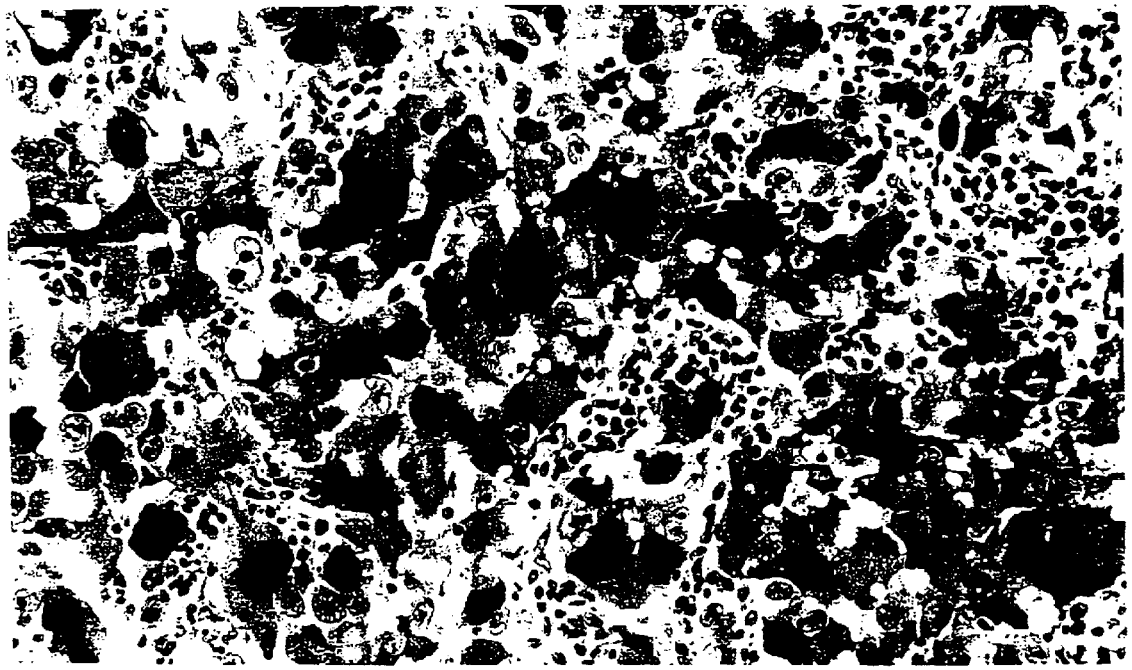

FIG. 9 is a photograph of SK-melanoma deposit in lymph node.

Panel A illustrates sections of the lymph node and show extensive replacement of the parenchyma by diffuse sheets of malignant melanoma cells.

Panel B shows variable mild to moderate predominantly cytoplasmic staining of tumour cells using the S100 preparation.

Figure 10A:
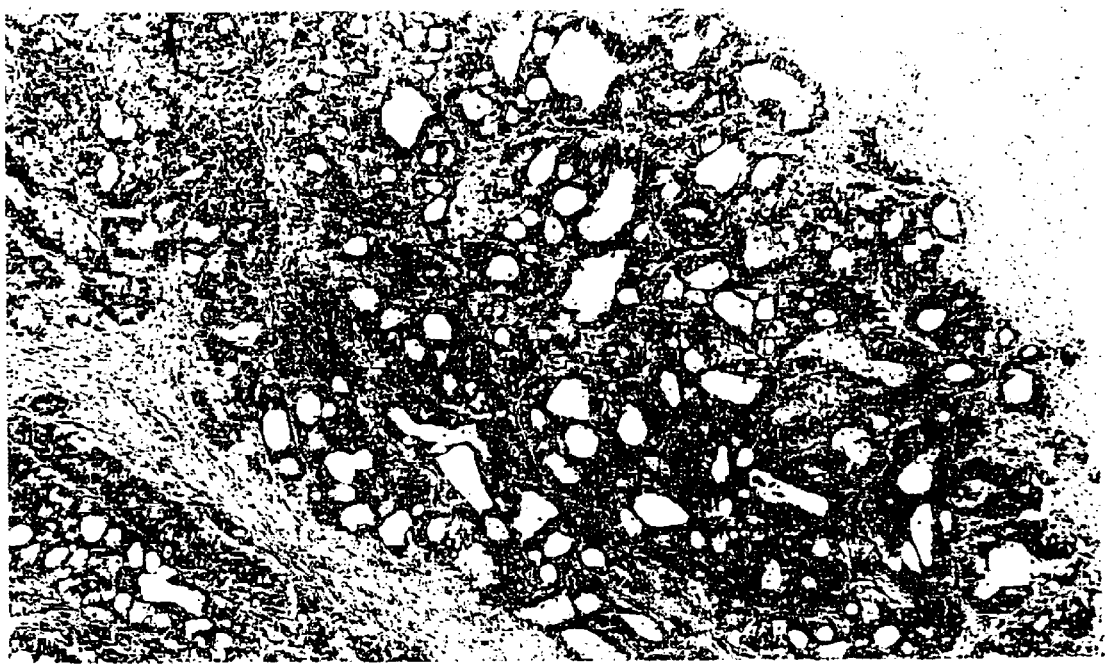
Figure 10B:
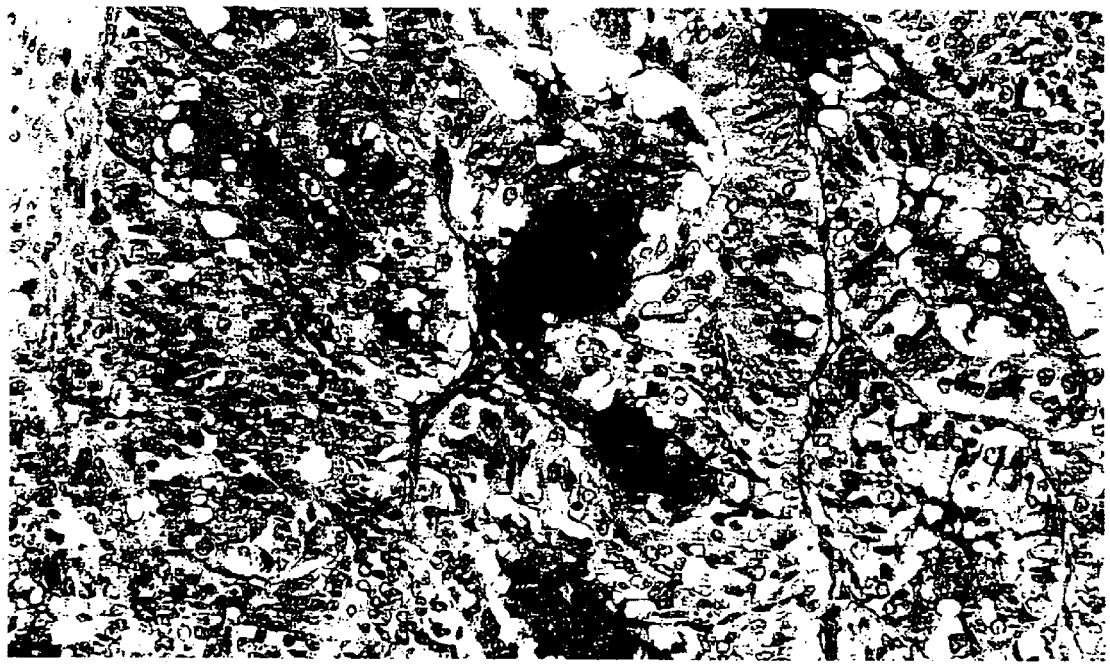
Figure 10C:
Figure 10D:
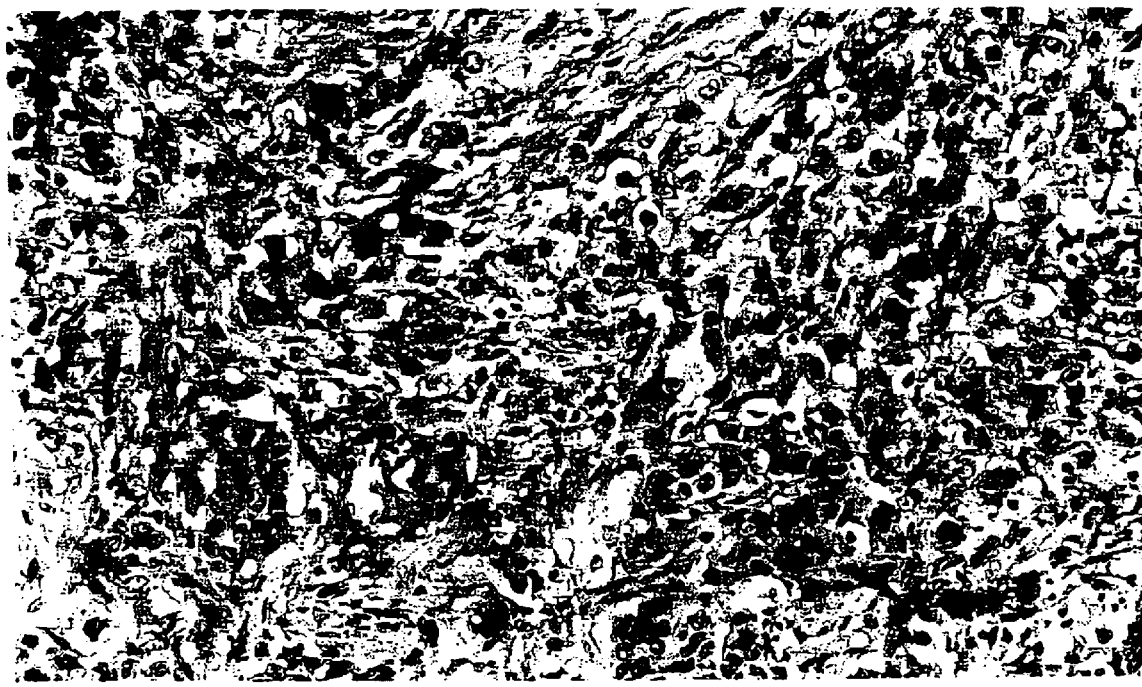
Figure 10E:
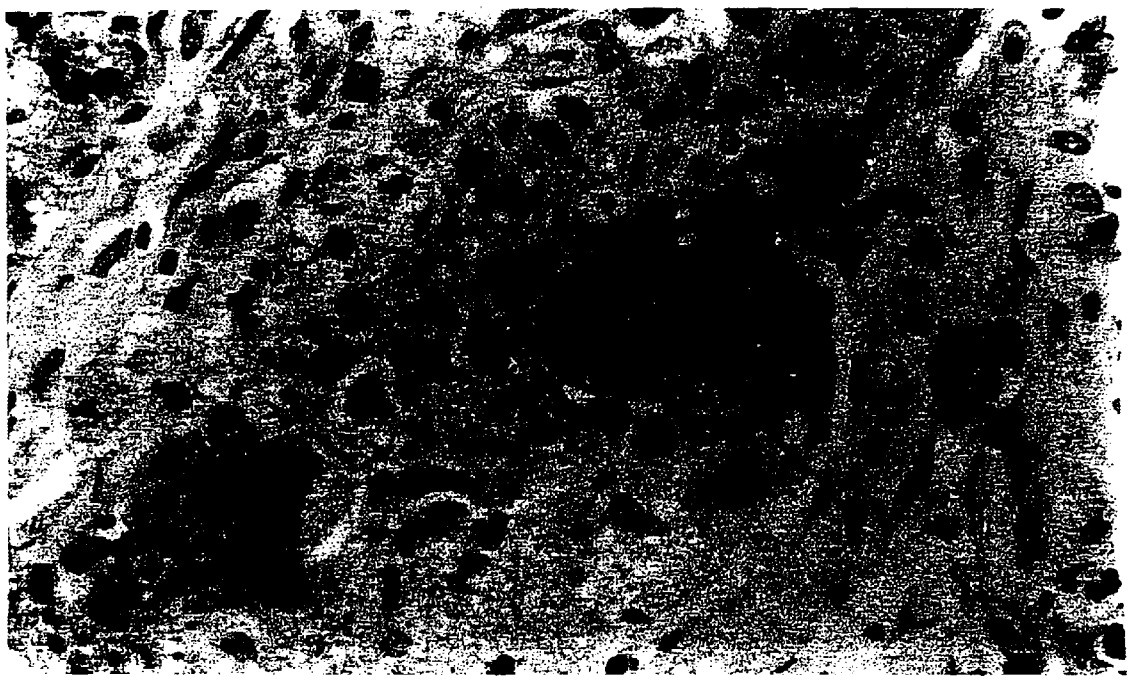
Figure 10F:

FIG. 10(i) is a photograph of skin deposit of adenocarcinoma LS174T.

Panel A shows well formed ancinar structures lined by tall columnar cells with moderate nuclear pleomorphism in the tumour. Mitotic figures are easily identified and there is mild focal necrosis with no significant inflammatory cellular exudate. Tumour infiltrating lymphocytes are infrequent (H&E).

Panel B represents abundant intraluminal PAS positive diastase resistant neutral mucin as seen with the PAS-D preparation.

Panel C shows immunostaining with Carcinoembryonic antigen. Marked positive, predominantly luminal staining with a lesser degree of granular cytoplasmic staining can be seen.

FIG. 10(ii) is a photograph of HT 29 adenocarcinoma deposit in skin.

Panel D shows that the tumour is poorly differentiated with little tendency towards acinar formation and is formed by predominantly sheet like arrangements of columnar and cuboidal cells with vesicular nuclei and prominent nucleoli. Mitotic figures are easily identified and there is focal necrosis and some peritumoural fibrosis. No significant inflammatory cellular response or tumour infiltrating lymphocytes are seen.

Panel E shows that a small amount of intraluminal PAS positive post diastase neutral mucin is seen in occasional acinar structures present. There are also intracytoplasmic mucin deposits, although this is not marked.

Panel F represents the immunoperoxidase preparation for CEA antigen which shows mild variable granular cytoplasmic staining with occasional "dot" like intracytoplasmic deposits.

The LS174T adenocarcinoma is well differentiated with prominent acinar formation, and exhibits marked mucinogenesis and marked positivity with CRA. In contrast, HT29 adenocarcinoma is poorly differentiated with only a mild degree of mucinogenesis and mild variable staining with CEA.

Figure 11:
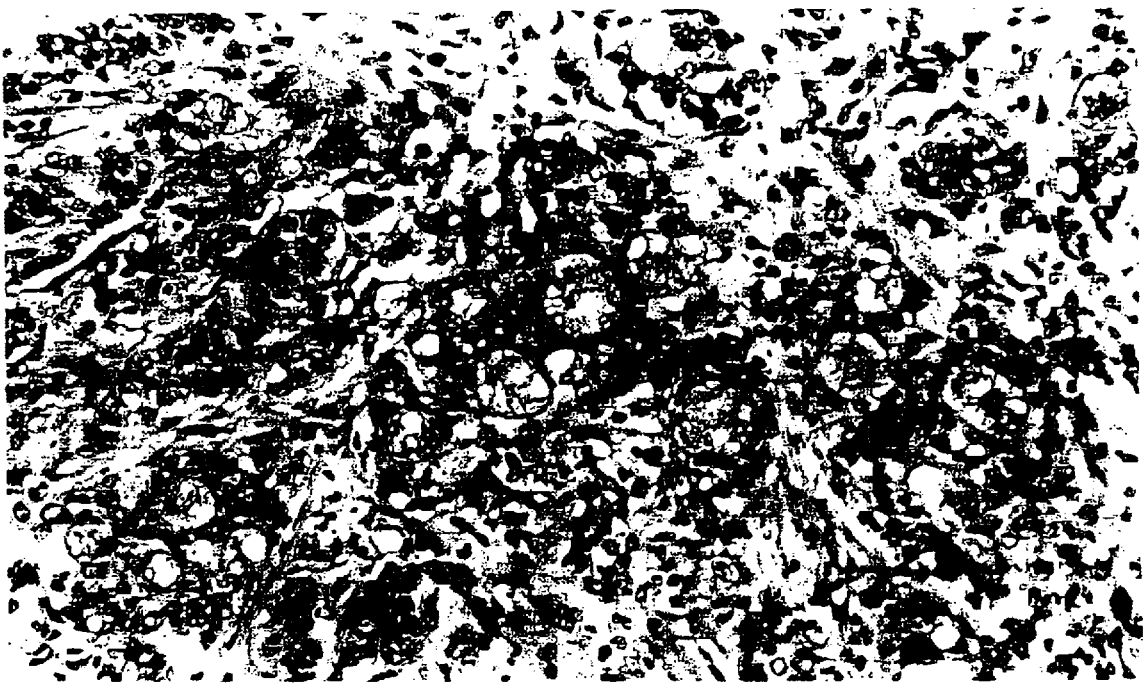

FIG. 11 is a photograph of LS174T adenocarcinoma deposit in intestinal wall.

There are deposits of moderate to well differentiated adenocarcinoma present beneath the mucosa showing some peritumoural fibrosis and a mild chronic inflammatory host response but no significant necrosis (H&E stain).

Figure 12:

FIG. 12 is a photograph of LS174T adenocarcinoma deposit in the liver.

There are deposits of moderately differentiated adenocarcinoma present associated with a mild to moderate degree of peritumoural fibrosis and a moderate chronic inflammatory cellular exudate is also seen. However, no significant necrosis or tumour infiltrating lymphocytes are present.

Figure 13A:
Figure 13B:
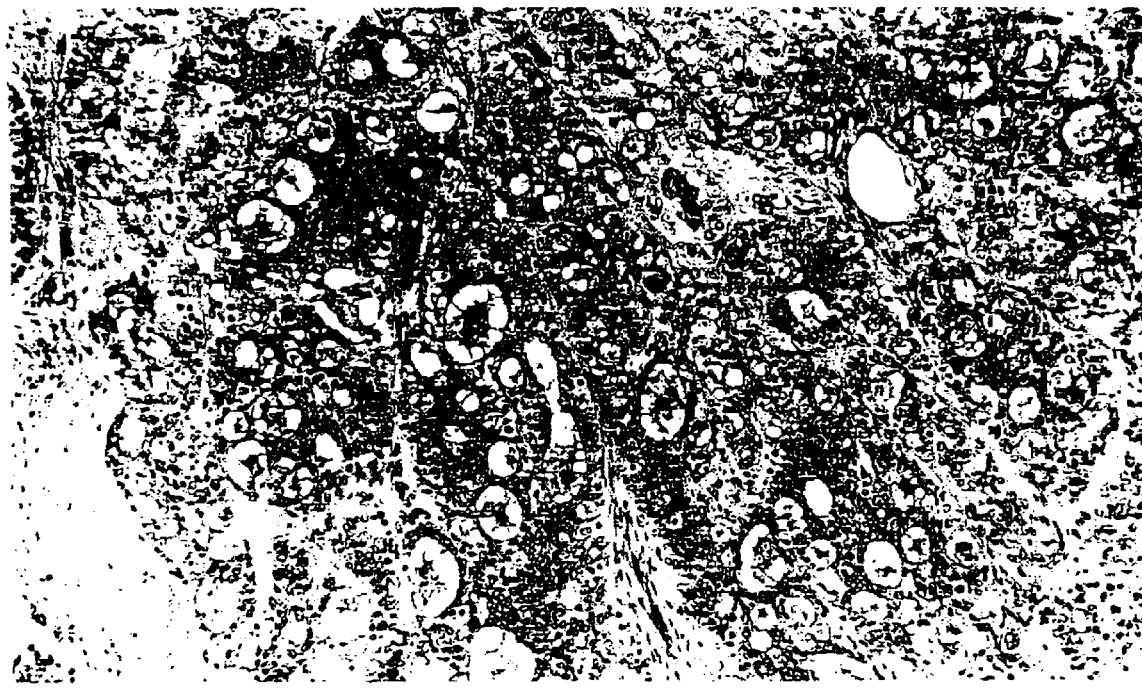
Figure 13C:
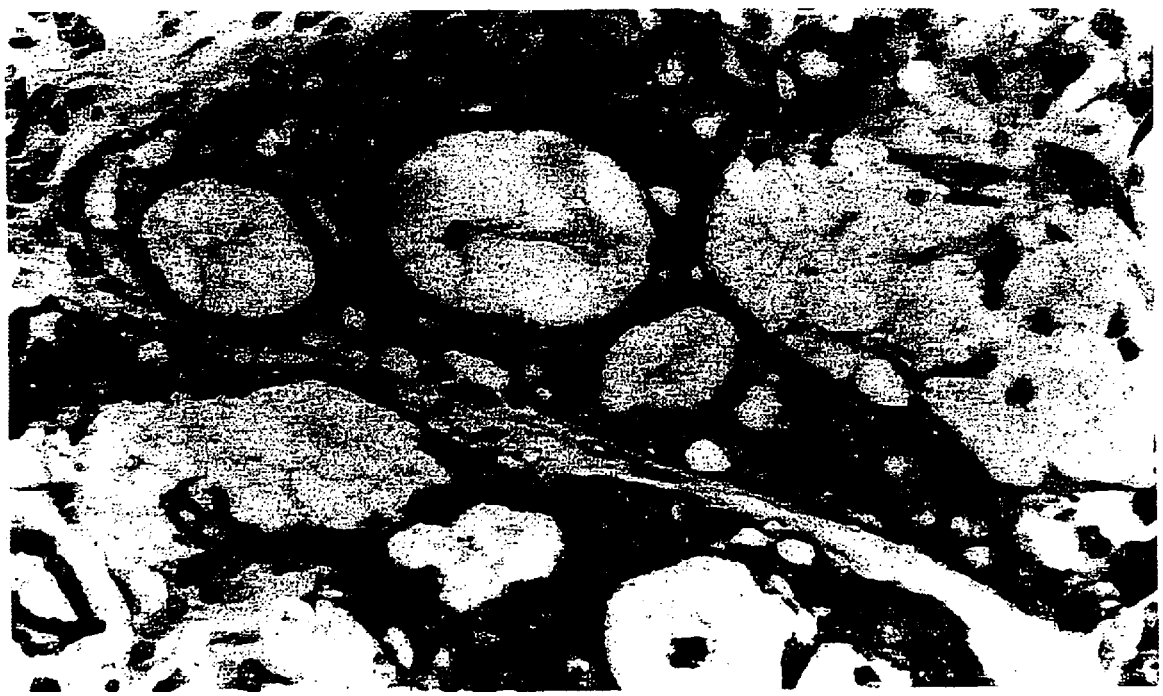

FIG. 13 is a photograph of LS174T adenocarcinoma deposit in peritoneal wall.

Panel A shows a tumour deposit with a well differentiated adenocarcinoma having prominent acinar formations lined by tall columnar cells with moderate nuclear pleomorphism and easily identifiable a typical mitoses. No significant necrosis is present and there is a mild peritumoural chronic inflammatory cellular exudate but no significant numbers of tumour infiltrating lymphocytes are seen (H&E stain).

Panel B shows abundant intraluminal PAS positive diastase resistant neutral mucin, seen with the PASD preparation.

Panel C shows immunostaining with Carcinoembryonic antigen, leading to marked positive, predominantly luminal staining as well as granular cytoplasmic staining.

Figure 14:
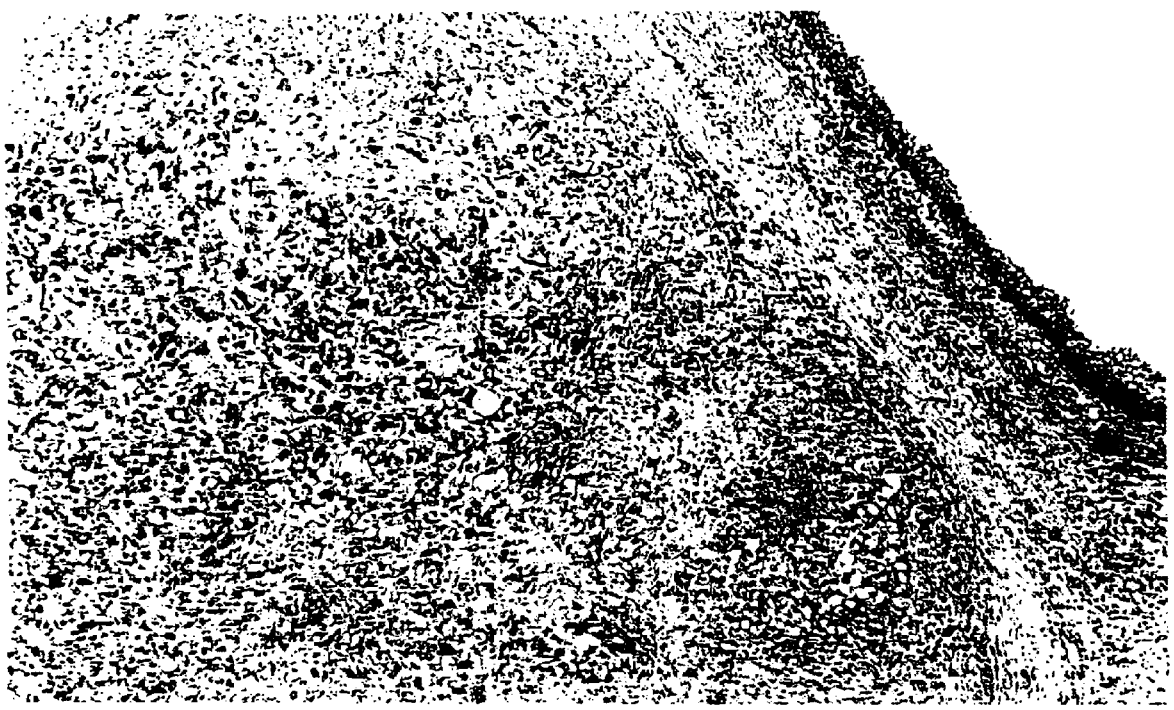
Figure 14:
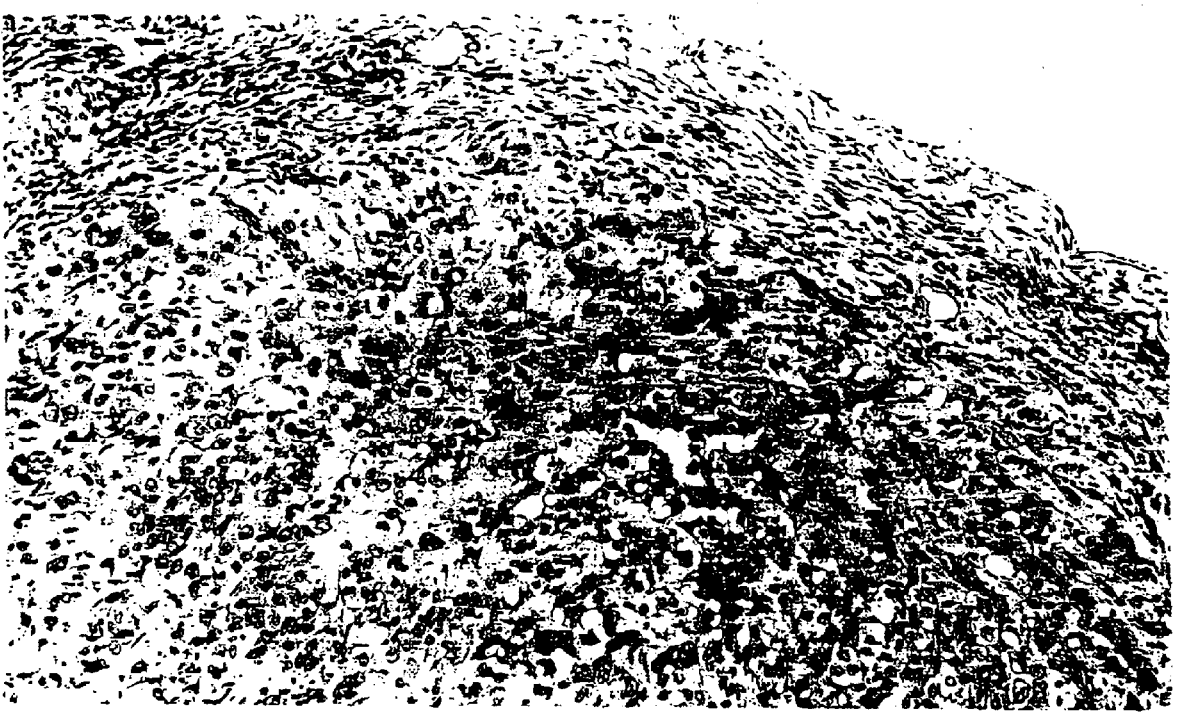

FIG. 14 is a photograph of JAM ovarian carcinoma deposit in ovary.

There are predominantly diffuse sheet like arrangements of pleomorphic malignant cells showing variable cytologic features. Tumour giant cells are prominent and there is moderate to marked nuclear pleomorphism with prominent a typical mitoses. No definite papillary structures are present and there is a mild peritumoural inflammatory host response and no significant tumour necrosis present.

Figure 15:
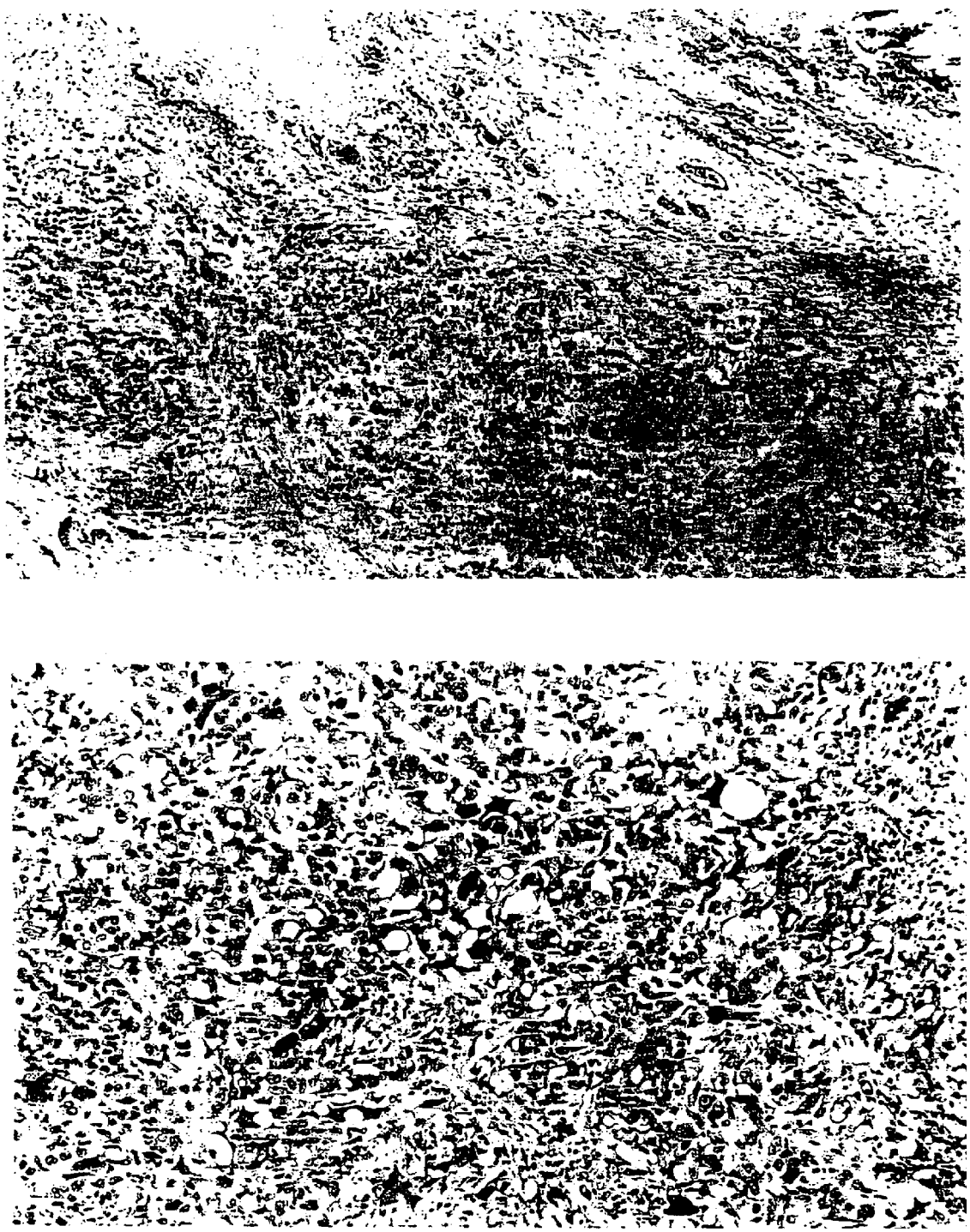

FIG. 15 is a photograph of JAM ovarian carcinoma in peritoneal wall. before dilution to 50 mg/ml with sterile saline. Before oral administration, crushed ketoconazole tablets were suspended in a drench vehicle which contained silicon dioxide (Ultrasil VN3 colloidal silicon dioxide, Degussa Australia Pty Ltd., Melbourne, Australia) gum xantham (Sigma), and polyethylene glycol 6000 (Sigma) in a citrate buffer.

Drugs

Acetonitrile was of hplc reagent grade. Fluoxetine hydrochloride was obtained from Eli Lilly Australia Pty, Ltd (West Ryde, NSW), CsA from Sandoz Australia (North Ryde, NSW), and ketoconazole from Janssen Cilag. All other chemicals were of analytical reagent grade.

Statistics

Data were analysed using the two-tailed Student's t test, unless otherwise stated.

EXAMPLE 1

Pharmacokinetics of CsA in Sheep; Effects of Coadministration of Ketoconzole

Surgical Procedure

Silastic catheters were placed to a depth of approximately 20 cm in both external jugular veins of Merino-Cross Dorset ewes under local anaesthesia, two days before drug administration commenced. Catheters were taped/sewn to the lateral surface of the neck, sealed with a three way tap, and protected with an elastic net bandage around the neck. One catheter was used for administration of CsA and the other for venous blood sampling. Catheters were flushed with sterile, heparinised saline twice daily to maintain patency.

There are diffuse sheets of poorly differentiated tumour similar to that described above, associated with a mild to moderate peritumoural chronic inflammatory cellular exudate and some fibrosis. No significant necrosis is seen and only small numbers of tumour infiltrating lymphocytes are present.

General Methods

Animals

Sheep

Mature Suffolk cross and Merino wethers were penned individually but at 4 to a room and were allowed to acclimatise for 10 days in an animal holding facility. The ad libitum diet comprised sheep cubes (Glen Forrest Stock Foods, WA.) supplemented by rough-cut chaff, hay and water. These animals were used for studying the pharmacodynamics and immunological effects of CsA and ketoconazole, and for implantation of cell lines.

Lambs

Merino-Dorset cross-lambs-of approximately 12 weeks of age, weighing around 25 kg and bred at Murdoch University, Murdoch, Western Australia, were housed in the same manner as the sheep.

Reagents

Cyclosporin A (CsA) was kindly donated by Sandoz Pharma Pty Ltd (Basel, Switzerland). The powder was dissolved in ethanol 1.75% v/v and polyethoxylated castor oil cremophor (BASF Chemicals, Melbourne, Australia) 3.25% v/v, then diluted to volume with sterile saline just prior to administration.

Ketoconazole was supplied as tablets (Nizoral, Janssen-Cilag, Lane Cove, NSW). Prior to administration by the intraperitoneal route, ketoconazole tablets were crushed and dissolved in a minimal volume of methanol Experimental Design and Blood Sample Collection Schedule CsA pharmacokinetics were studied after the first dose (3 mg/kg iv) and again at steady-state when the animals had been receiving CsA (3 mg/kg iv) and ketoconazole (10 mg/kg po) for 18 days. Following the first dose on the first study day, venous blood samples (5 ml, anticoagulated with EDTA) were collected at 0.17, 0.33, 0.5, 0.75, 1, 2, 3, 4, 6, 8, 12, 15, 22, 27 and 32 h. Following this initial study, twice daily administration (dose interval τ=12 h) of CSA and ketoconazole was commenced. Blood samples for CsA analysis were obtained twice weekly, just before the morning doses, over the next 18 days. Animals were weighed twice weekly and absolute drug doses were modified to maintain the initial dose rates in mg/kg. on day 18, when the CsA blood concentrations had reached steady-state, the final CsA dose was administered and blood samples were again collected at 0.17, 0.33, 0.5, 0.75, 1, 2, 3, 4, 6, 8, 12, 15, 24, 30, 36, 48, 56, 72, 96 and 144 h. Ketoconazole administration was continued throughout the latter blood sampling period.

Analysis of CsA and Ketoconazole

For routine monitoring of blood CsA concentrations during the experimental period, CsA in whole blood was measured by enzyme multiplied immunoassay (EMIT®, Syva Company, Evergreen, Calif.) as previously described (Dusci et al, 1992). Blood samples were then frozen at −20° C. and at the end of the experiment were analysed by high performance liquid chromatography (hplc) as previously described (Dusci et al, supra). Only hplc-derived data were used for subsequent pharmacokinetic analyses.

Some blood samples taken on days 18–23 were centrifuged to yield plasma which was frozen at −20° C. until analysed for ketoconazole by a specific hplc method. Aliquots of plasma (0.1 ml) were vortexed vigorously with 1 ml acetonitrile (containing 8 mg of fluoxetine hydrochloride as internal standard) for 15 sec. The mixture was centrifuged at 1200 g for 10 min to sediment proteins, 0.5 ml of the supernatant was aspirated, transferred to a clean tube and evaporated to dryness at 50° C. using dry $N_2$. The extract was reconstituted in 0.2 ml of hplc mobile phase and 0.02 ml aliquots were injected onto the hplc column. The hplc system consisted of a Merck RP Select B C18 column (25 cm×4.6 mm id), a mobile phase of 55% acetonitrile in 0.01% v/v $H_3PO_4$ and 0.01% W/V NaCl. The solvent was pumped at a flow rate of 1.5 ml/min and eluting compounds were detected by their UV absorbence at 210 nm. The assay was linear over the range 0.5–33 mg/l with a detection limit of 0.2 mg/l. The within-day coefficients of variation at 2, 5.6 and 22 mg/l were 3.6, 6.8 and 3.0% respectively (n=5). The between-run coefficient of variation at 2 mg/l was 9.8% (n=5).

Pharmacokinetic Analyses

Whole blood concentration-time data for cyclosporin were analysed by a noncompartmental pharmacokinetic method using the program TOPFIT (Thomann, 1993). The terminal elimination rate constant ($\lambda_z$) was estimated by log-linear least squares regression of the last 6–8 concentration-time data points. Areas under the plasma-concentration time data and ($AUC_{O12}$ at steady-state and/or $AUC_{0-\infty}$) were measured by the linear trapezoidal rule with area from the last measured concentration to infinity being estimated as $C_{p\ last/Ke}$. Plasma clearance (CL=dose/AUC), mean residence time (MRT=AUMC/AUC and $MRT_{ss}$= {$AUMC_{0-\tau}$+τ$AUC_{(\tau-\infty)}$}/$AUC_{(0-\tau)}$), volume of distribution ($V_z$=CL/$\lambda_z$), and volume of distribution at steady-state ($V_{ss}$= MRT*CL) were estimated from the whole blood data as appropriate. Results have been summarised as mean (95% confidence interval). Differences between means were assessed by a paired t test, at the 0.05 level of significance.

Results

Correlation Between EMIT and hplc Methods of Analysis

Figure 1:
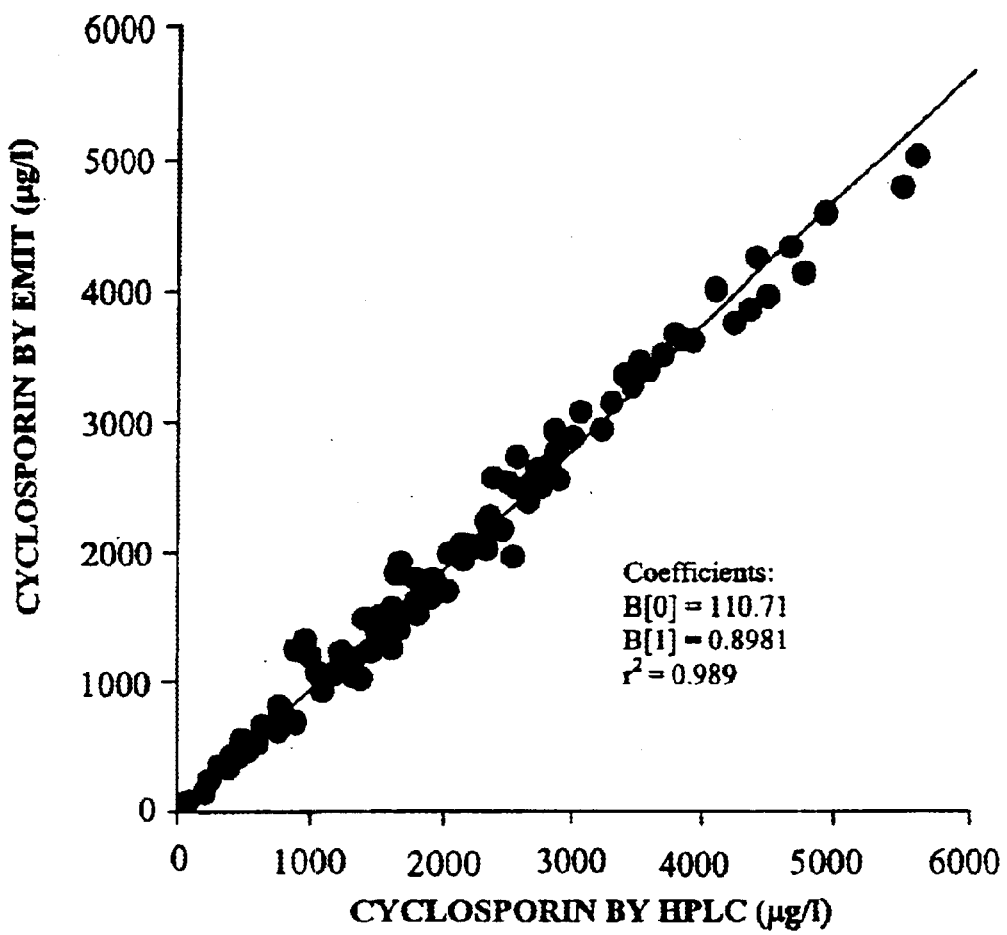
FIG. 1 is a correlation plot for CSA concentration estimated in 136 blood samples by enzyme multiplied imnunoassay (EMIT®) and by high performance liquid chromatography (hplc). The solid line shows the line of best fit as calculated by linear regression.
Figure 2:
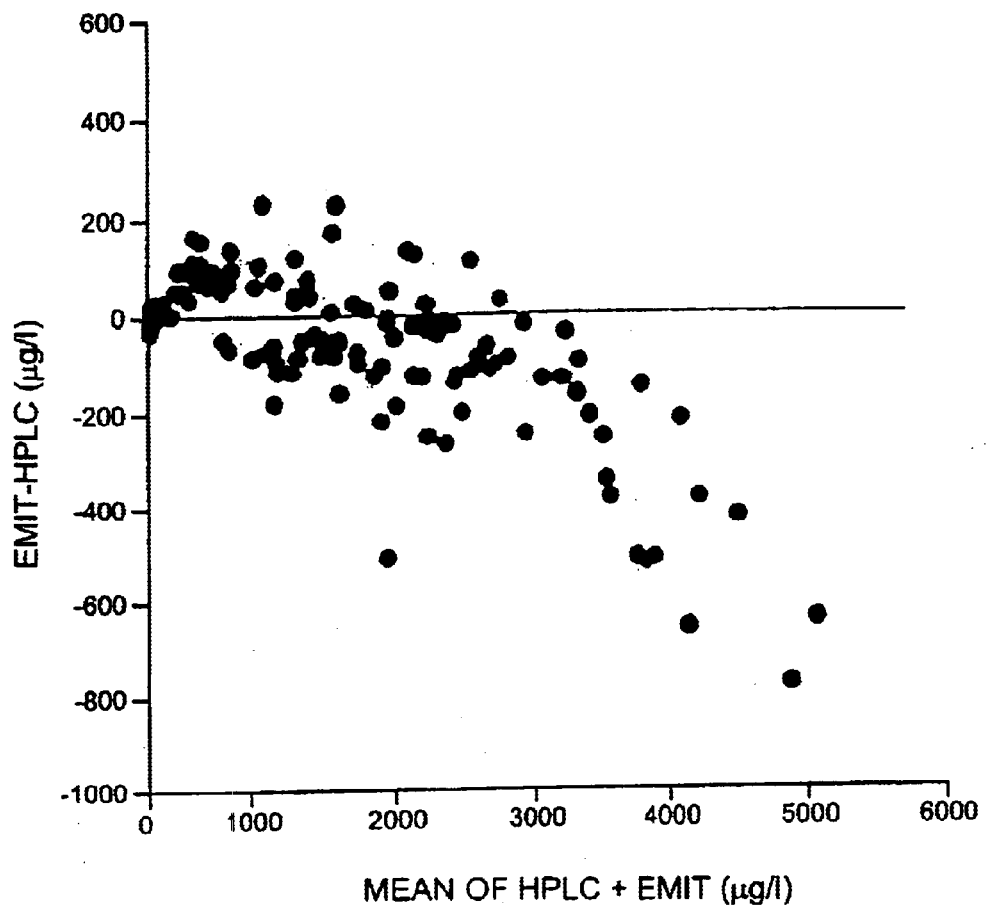
FIG. 2 shows the relationship between the difference between CsA concentration estimated by EMIT and hplc (y-axis) versus the mean of the concentrations measured by EMIT and hplc (x-axis).

FIG. 1 shows that there was a significant correlation (EMIT=0.8981×hplc+110.7; $r^2$=0.989) between CsA concentrations in 136 blood samples measured by the EMIT immunoassay system and by the specific gold standard hplc method. However, when the data are critically analysed using the plot of the difference between the two methods versus the average of the EMIT and hplc methods (FIG. 2; Bland and Altman, 1986), it is apparent that the EMIT method performs satisfactorily up to around 2000 μg/l, but at greater concentrations, it consistently underestimates the true concentration. The reason for this discrepancy has not been identified, but differences in the ratio of CsA to its metabolites between low (mainly from the first study on day 0) and high (mainly at steady-state with ketoconazole present) CsA concentrations may be a modulating factor in the specificity of the test kit antibodies. While the nature of the difference between these two methods for CsA assay in sheep blood is different to that which we have previously reported for human blood (Dusci et al, 1992), the data indicate that the specificity of immunoassay methods is often questionable. Thus, only concentration measurements made by a specific hplc method are satisfactory for pharmacokinetic analyses. Nevertheless, we consider that the EMIT method is adequate for rapid routine monitoring of trough concentrations of CsA in the immuno-suppressed sheep model, particularly as we have found that these concentrations should be maintained in the range of 750–1500 ng/l.

Steady-State Concentrations of Ketoconazole

Steady-state concentrations of ketoconazole were measured in plasma from 5–8 trough blood samples obtained from the sheep on days 18–23 of the study. Mean concentrations were 2.6, 2.19, 1.63 and 3.04 mg/l in sheep 14 through 17 respectively.

Pharmacokinetics and Steady-state Concentrations of CsA Before and During Retoconazole Coadministration Following regular dosing with CsA and ketoconazole twice daily, trough blood CsA concentrations increased slowly and plateaued after about 2 weeks. Mean trough concentrations for the 4 sheep were 925, 1163, 954, 1694 and 1906 μg/l on days 3, 8, 10, 13 and 18 of treatment. Typical plasma concentration-time profiles for sheep #14 after the first dose and at steady-state are shown in FIG. 3. Mean pharmacokinetic data for all 4 animals are summarised in Table 1. At steady-state, half-life and MRT were significantly increased (P<0.007) and CL was significantly decreased (P<0.007) compared to the values for the first dose. Both $V_z$ and $V_{ss}$ were similar after the first dose and at steady-state in the presence of ketoconazole.

TABLE 1

Pharmacokinetic descriptors for cyclosporin (3 mg/kg iv) after the first dose alone, and at steady-state during the coadministration of ketoconazole (10 mg/kg po).

| CsA | $t_{1/2}$ (h) | MRT (h) | CL (ml/min/kg) | $V_z$ (l/kg) | $V_{ss}$ (l/kg) |
|---|---|---|---|---|---|
| First dose | 14.7 (5.1–24.3) | 12.6 (4.2–21.0) | 9.47 (6.2–12.7) | 11.5 (5.5–17.5) | 6.9 (2.8–11.0) |
| Steady-state | 72.0* (38.6–105.4) | 75.4* (41.8–109.0) | 1.62* (1.38–1.86) | 10.1 (5.5–16.3) | 7.3 (4.1–10.5) |

Data as mean (95% CI);
*P < 0.007 for paired t-test between parameters for first dose and steady-state Summary The inhibition of CSA metabolism by other drugs was first noted through drug interaction studies (Yee, 1990). More recently, there have been several clinical studies which have shown that coadministration of either the competitive inhibitor ketoconazole (First et al, 1993; Patton et al, 1994; Keogh et al, 1995) or the competitive substrate diltiazem (Smith et al, 1994; Valantine et al, 1992; Wahlberg et al, 1992) has a substantial dose-sparing action on CsA in transplant patients.

Our values for MRT, CL and $V_{ss}$ for CsA following the first dose were comparable to those reported by Charles et al (1993). Our study is the first to show that coadministration of ketoconazole significantly decreases the CL of CsA in the sheep. MRT was significantly reduced (approximately 6-fold), $V_{ss}$ was unchanged, and there was a corresponding significant decrease in CL. These changes are consistent with data for the iv use of CsA in humans (Gomez et al, 1995). Thus, we conclude that ketoconazole can be used successfully as a CsA sparing agent in the sheep model.

EXAMPLE 2

In vivo/In vitro Assessments of Single Dose Pharmacodynamics and Immunological Effects of CsA and Ketoconazole in Sheep.

Treatment Procedure

On the day on which drug treatment was initiated, each sheep was fitted with an intrajugular cannula to facilitate the taking of blood samples. Cannulae remained in situ for 24 to 48 hours only and were maintained with a solution containing heparin, penicillin and streptomycin and were flushed with sterile saline prior to taking blood samples for pharmacokinetic studies. CsA was given by injection into the opposite external jugular vein and subsequent blood samples for lymphocyte culture were obtained by venipuncture from the opposite external jugular vein. In pharmacokinetic studies, blood was sampled in EDTA collection tubes immediately before administration of CsA and at intervals of 20 min, 30 min, 45 min, 60 min, 1.5 hours, 2 hours, 3 hours, 6 hours, 9 hours, 12 hours, 24 hours, 36 hours and 48 hours after receiving CsA. Heparinized blood samples for lymphocyte function assays were collected before administration of CsA (Day 0) and at 24 hours, 48 hours, 72 hours, 5 days and 7 days after receiving CsA. Where ketoconazole was administered in combination with CsA, intraperitoneal (ip) ketoconazole (5 mg/kg) was commenced one day prior to CsA, or oral ketoconazole (10 mg/kg) was commenced two days prior to CsA, to allow for an effect on the liver before exposure to CsA.

CsA Assay

Levels of CsA in peripheral blood were measured using the CsA Monoclonal Whole Blood fluorescence polarization immunoassay system (Abbott Diagnostics, Abbott Park, Ill., USA) and read on a TdX autoanalyser.

Lymphocyte Preparation

Lymphocytes were prepared from heparinized whole blood collected between 8.30 and 10 am on each test day. The leucocyte-rich buffy coat layer was collected after separation, diluted with phosphate buffered saline (PBS), and applied to Ficoll-hypaque (Pharmacia, North Ryde, NSW) density gradients to obtain lymphocyte preparations. After two low-speed washes with PBS, the lymphocyte preparations were resuspended in RPMI 1640 medium (Flow Laboratories, Australia Biosearch, Karrinyup, Australia) supplemented with 10% foetal calf serum (FCS, Cytosystems, Sydney, Australia) and penicillin (100µ/ml) before counting and confirmation of viability.

Mitogen Stimulation Assays

The capacity of lymphocytes to proliferate in response to in vitro stimulation by Phytohaemagglutinin A (PHA; Sigma), Concanavalin A (ConA; Sigma) and Pokeweed Mitogen (PWM; Sigma) was assessed. Lymphocytes were seeded into 96-well flat bottom tissue culture plates (Disposable Products, Adelaide, South Australia) at a concentration of $10^5$ cells/well. Mitogens (PHA, ConA, and PWM) were added to triplicate wells to obtain concentrations of 10 µg/ml of each mitogen. Plates were incubated at 37° C. in 5%$CO_2$ for 48 hours before labelling with 1 MBq/well of $^3$H-thymidine (Amersham, Melbourne, Australia). Cultures were harvested on to glass filters 24 hours after labelling using an automated cell harvester (PHD, Cambridge Technology, USA) and $^3$H incorporation determined by liquid scintillation counting using a Minaxi tri-Carb 400 beta counter (United Technology/Packard). Results were expressed as change in counts per minute (Δcpm), constituting the mean cpm of triplicate stimulated wells minus the mean cpm of triplicate background wells without added mitogen.

Mixed Lymphocyte Cultures

The ability of isolated lymphocytes to respond to allogeneic tissue antigen was assessed by mixed lymphocyte culture (MLC). Lymphocytes obtained as described above from test sheep were adjusted to $2.5 \times 10^5$/well in 96-well flat bottom tissue culture plates. An equal number of lymphocytes isolated from an unrelated untreated donor sheep were subject to 20 Gray (Gy) of X-irradiation and added to triplicate or quadruplicate wells as stimulator cells. Irradiated lymphocytes from each individual test sheep were also prepared and set up against homologous responder cells to obtain individual background data. Controls to confirm adequacy of inactivation by X-irradiation were also included in each assay.

Mixed lymphocyte cultures were incubated at 37° C. and 5% $CO_2$ for 6 days before overnight labelling with $^3$H-thymidine and harvesting as described above. Stimulation indices were determined by dividing the mean cpm of the wells containing test lymphocytes co-cultured with X-irradiated stimulator cells by the mean cpm of the background wells utilizing X-irradiated and non-irradiated homologous cells.

FACS Analysis

Lymphocytes prepared as described above were adjusted to 1 to $3 \times 10^6$/well in 96—well round bottom culture plates (Disposable Products, Adelaide, South Australia) and incubated overnight at 4° C. with monoclonal antibodies to lymphocyte marker antigens at a final dilution of 1/100. A panel of monoclonal antibodies defining ovine lymphocyte surface markers (Hein et al, 1991) was obtained from the Centre for Animal Biotechnology, The University of Melbourne, Parkville, Australia. The monoclonal antibodies used were SBU-LCA (detecting CD45, leucocyte-common antigen), SBU-T1 (CD5, all T cells), SBU-T4 pool (CD4, T helper cell subset), SBU-T8 (CD8, T suppressor/cytotoxic subset) and SBU-T19 (defining the CD4–CD8-gamma delta T cell subset in sheep, currently of unknown function). B lymphocytes were identified by surface immunoglobulin expression.

The following day, plates were washed three times with PBS and incubated with fluorescein-conjugated anti-mouse Ig (Silenus Laboratories, Hawthorn, Australia) at 1/100 dilution for 1 hour at 37° C. B cells were labelled by incubation with fluorescein-conjugated donkey anti-sheep Ig (Silenus Laboratories, Hawthorn, Australia) at 1/100 dilution. After a further three washes in PES, 50 μl of PBS containing 1% formalin was added to each well and the plates stored in the dark at 4° C. until FACS analysis was carried out using an EPICS Profile Analyser (Coulter Corporation, Hialeah, Ill., USA).

Biochemistry

Blood samples were taken daily over the course of the experiments for assessment of serum albumin, bilirubin, alkaline phosphatase, gamma glutamyltransferase (GGT), alanine aminotransferase (ALT), creatine, urea, and electrolytes to indicate liver and kidney function.

Statistics

Pharmacokinetic parameters were calculated by standard methods of curve fitting using the "MINIM" software package and a Macintosh computer. Area under the blood concentration-time curve (AUC) and the area under the first moment blood concentration-time curve (AUMC), mean residence time (MRT), steady state volume of distribution and total clearance were calculated by standard methods (Gibaldi, 1991).

Results

Pharmacodynamics

The mean absorption time, half-life and steady state volume distribution of CsA were comparable to those from humans (Gupta et al., 1987, Charles et al., 1993).

Ketoconazole significantly altered the AUC by reducing CsA clearance, leading to a two-fold increase in AUC after an oral dose of ketoconazole 10 mg/kg ($p<0.05$, Dunnett's test; 24,4 d.f.) the AUC following a dose of 2.5 mg/kg of CsA with 10 mg/kg ketoconazole po was slightly greater than that following 5 mg/kg CsA alone, as shown in FIG. 4. Administration of ketoconazole either ip or po along with a halved dose (2.5 mg/kg) of CsA maintained the AUC at a level similar to that achieved with the full dose of 5 mg/kg dose of CsA alone.

The pharmacokinetic parameters of CsA and ketoconazole, calculated using AUC and AUMC are shown in Table 2 and also FIG. 4.

TABLE 2

| Treatment Group | n | Total clearance 1/h/kg | Steady state distribution volume 1/kg | AUC ng/ml. h | MRT h | Half life h | Relative AUC* % |
|---|---|---|---|---|---|---|---|
| CsA 5 mg/kg IV | 8 | 0.498 ± 0.024 | 5.719 ± 0.267 | 10183 ± 4.55 | 11.60 ± 0.63 | 8.04 ± 0.44 | |
| CsA 5 mg/kg IV plus Ketoconazole 5 mg/kg IP | 6 | 0.358 ± 0.036 | 4.390 ± 0.467 | 14698 ± 1505 | 12.50 ± 1.28 | 8.66 ± 0.88 | 144.3 |
| CsA 2.5 mg/kg IV plus Ketoconazole 5 mg/kg IP | 6 | 0.337 ± 0.045 | 2.447 ± 0.175 | 8049 ± 965 | 7.82 ± 0.97 | 5.42 ± 0.67 | 158.0 |
| CsA 2.5 mg/kg IV plus Ketoconazole 10 mg/kg PO | 6 | 0.247 ± 0.012 | 3.490 ± 0.238 | 10257 ± 536 | 14.08 ± 1.23 | 9.75 ± 0.85 | 201.0 |

*Dose-corrected AUC relative to CsA 5 mg/kg IV

Mitogen Responses

Figure 5A:
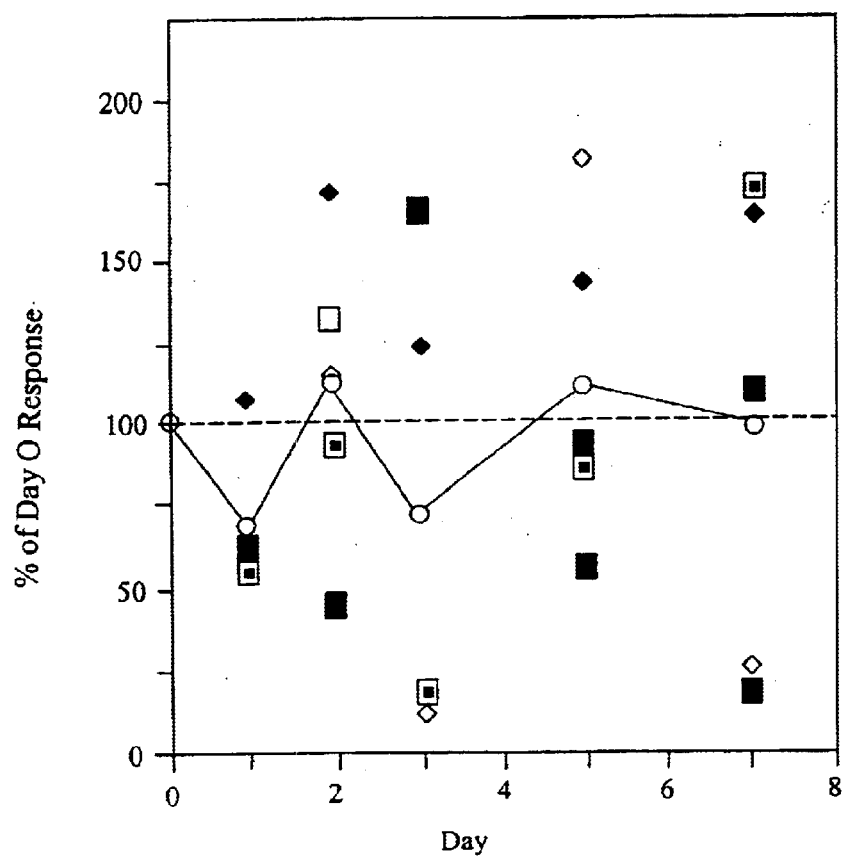
Figure 5B:
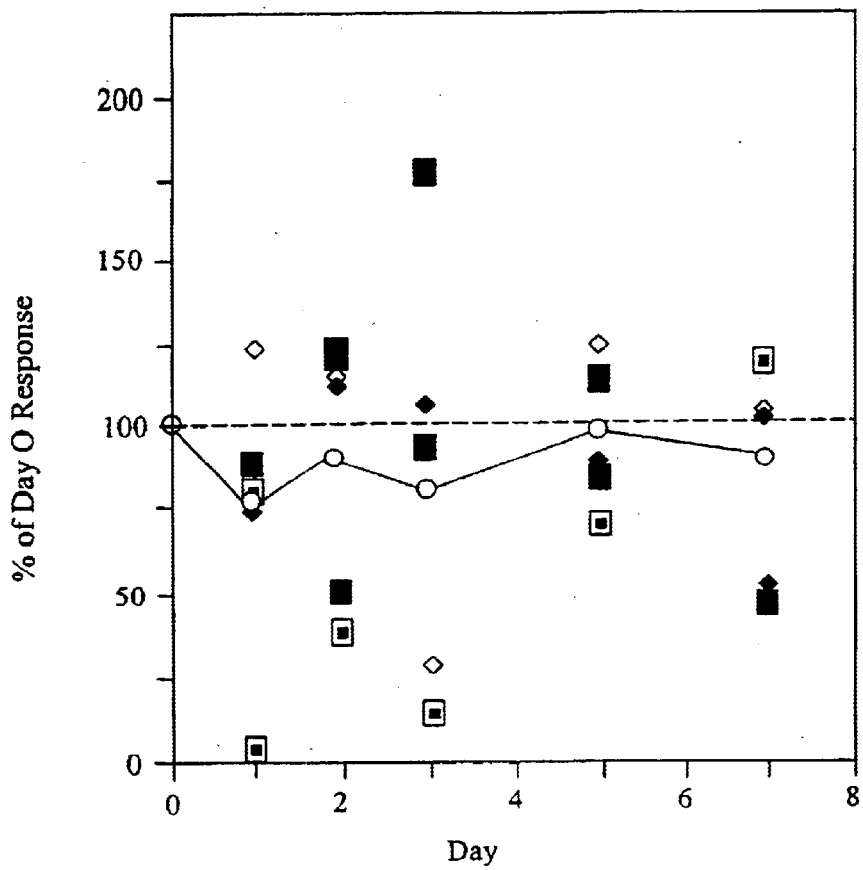
Figure 5C:
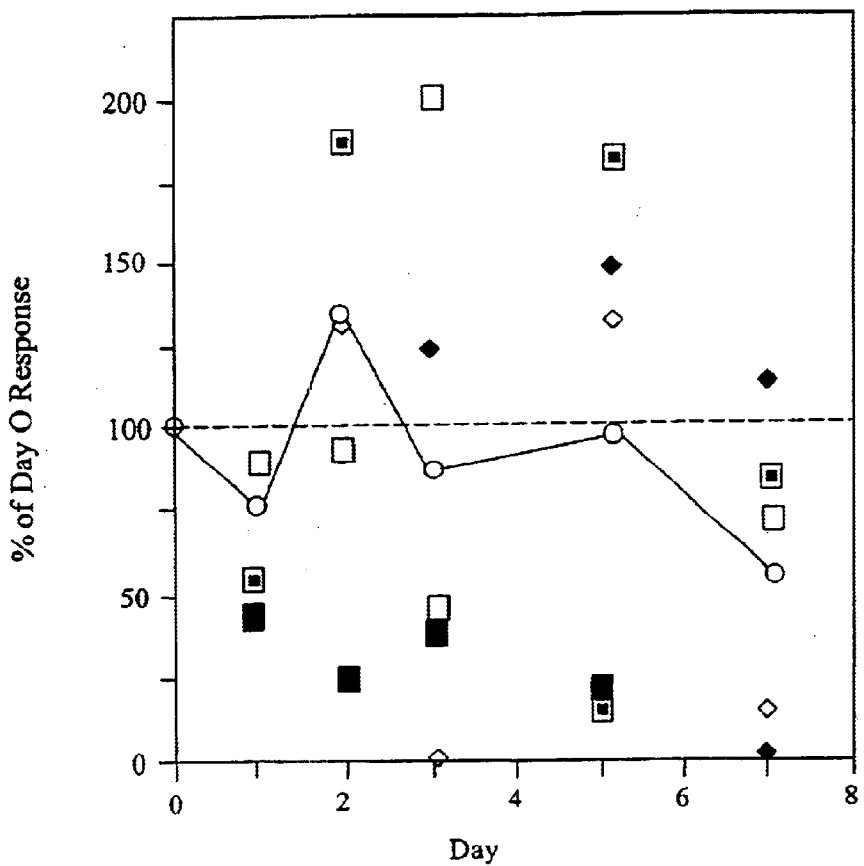

Mitogen proliferation data from sheep receiving CsA 5 mg/kg alone iv are shown in FIG. 5(a), (b) and (c). The data show that there was a transient suppression of lymphocyte response at 24 hour.

Figure 5D:
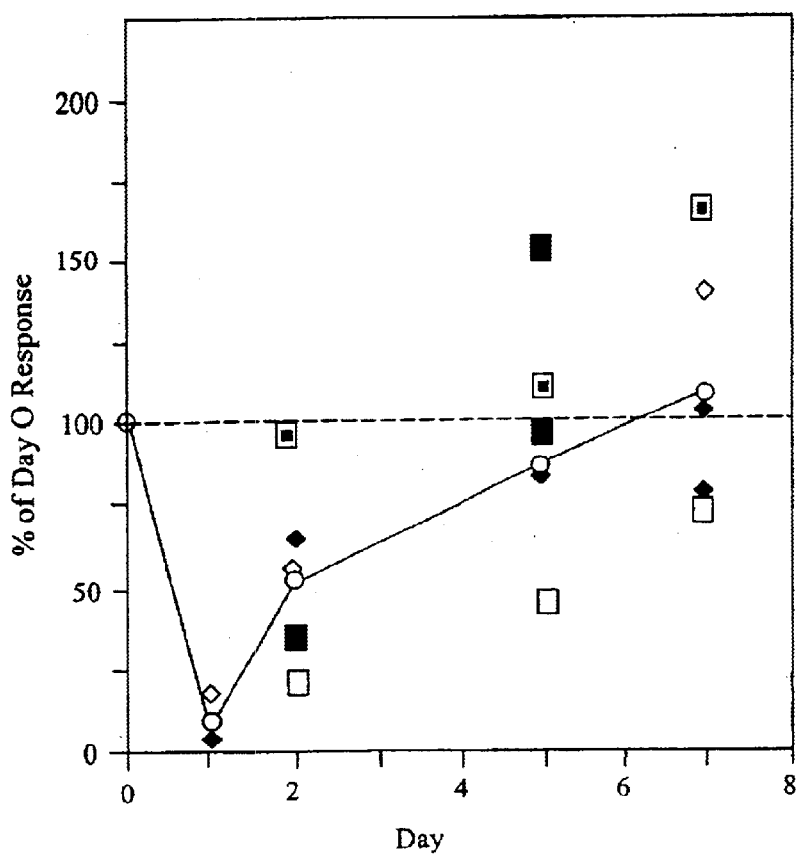
Figure 5E:
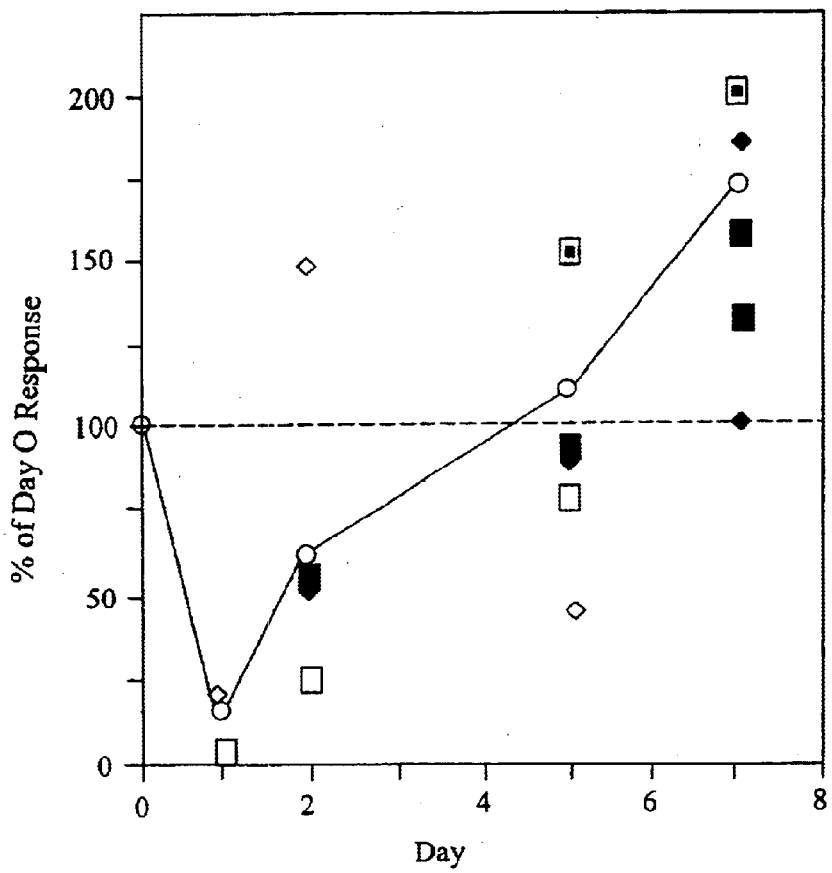
Figure 5F:
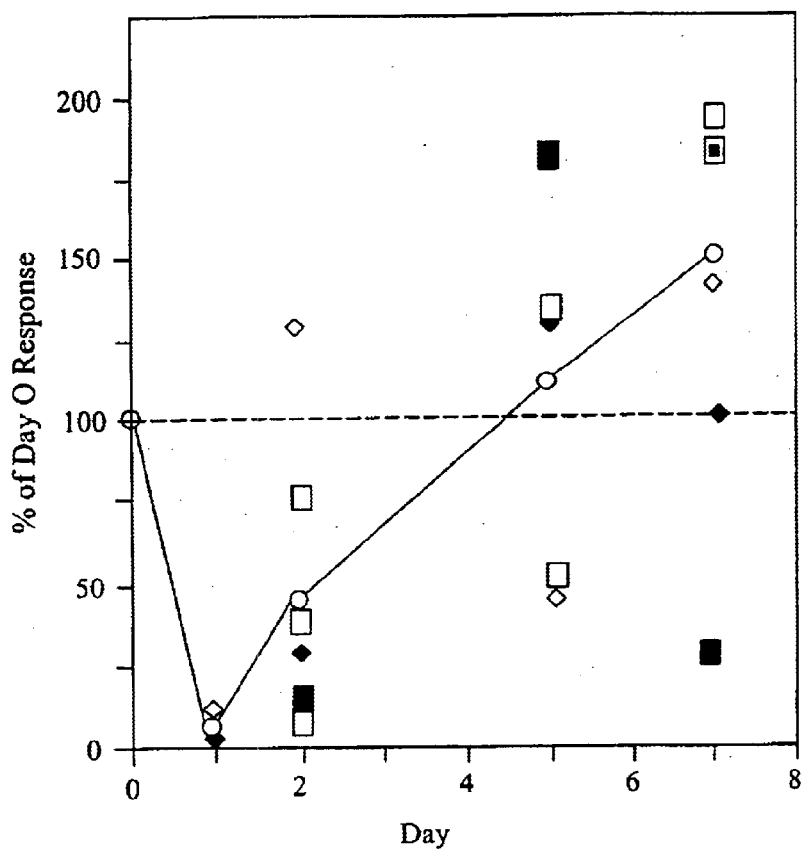

The concomitant ip administration of ketoconazole 5 mg/kg and CsA iv 5 mg/kg markedly potentiated the depression of lymphoproliferative responses to all mitogens tested (FIGS. 5(d), (e) and (f)). Normal reactivity to mitogens was regained at 48 hours in sheep, treated with CsA alone. In CsA+ketoconazole treated sheep responses substantially recovered by 48 hours.

A correlation between CsA AUC values and depression of mitogen response was observed when comparing the CsA and the CsA+ketoconazole treated groups ($p<0.05$)

MLC Responses

MLC responses were not significantly different from Day 0 at 48 hours, 72 hours or 7 days, ($p>0.05$, Wilcoxon Signed Rank test, n=6). However lymphocyte responses were significantly elevated, relative to Day 0, at 5 days after receiving CsA ($p<0.05$, Wilcoxon Signed Rank test, n=6).

Lymphocyte Phenotypes

In sheep receiving CsA 5 mg/kg alone by the iv route numbers of circulating $T1^+$ cells were slightly elevated at 48 hours ($p<0.05$, Student's t test, 2 d.f); the T4:T8 ratio remained unchanged.

In the experimental group receiving CsA 5 mg/kg i.v and ketoconazole ip, the total number of T cells (T1+) did not alter significantly but a significant increase in the number of circulating T4 positive lymphocytes was observed. Likewise T4:T8 ratios were elevated. These results are summarized in Table 3.

TABLE 3

Lymphocyte Subsets after Combined CsA and Ketoconazole Surface Antigen

|  | LCA | T1 | T4 | T8 | T119 | Slg |
|---|---|---|---|---|---|---|
| 0 hrs | 98.7 ± .92 | 62.3 ± 12.7 | 7.64 ± 1.76 | 4.9 ± 1.76 | 23.8 ± 7.2 | 19.6 ± 15.1 |
| 24 hrs | 94.8 ± 6.6 | 54.1 ± 17.7 | 11.9 ± 2.4 | 9.0 ± 4.6 | 26.4 ± 5.9 | 22.6 ± 14.4 |
| 48 hrs | 87.9 ± 11.3 | 49.3 ± 8.2 | 13.7 ± 2.2 | 7.3 ± 2.6 | 26.4 ± 5.9 | 27.3 ± 11.7 |
| 72 hrs | 92.0 ± 0.8 | 58.0 ± 9.2 | 13 ± 3.8 | 6.8 ± 2.1 | 20.4 ± 7.6 | 8.35 ± 6.6 |
| 5 days | 97.3 ± 1.1 | 67.7 ± 6.9 | 11.85 ± 1.4 | 6.05 ± 1.94 | 20.8 ± 4.6 | 12.9 ± 7.7 |
| 7 days | 98.7 ± 2.6 | 63.3 ± 12.4 | 17.9 ± 3.1 | 6.6 ± 1.4 | 18.98 ± 3.8 | 32.2 ± 11.1 |

(% fluorescent cells mean ± SD n = 6)

SUMMARY

These results demonstrate that a single dose of CsA effectively suppressed lymphocyte responses in the sheep, and that the effect of concomitant ketoconazole administration on CsA kinetics in the sheep parallels that seen in humans.

Co-administration of CsA with ketoconazole was effective in suppressing T cell immunity in the sheep, and a single-dose regimen was well tolerated, without apparent adverse reactions.

Example 3

Effects of CsA and Ketoconazole on Tumour Cell Growth in vitro

Prior to initiating tumour xenograft transplantation in a sheep model, the susceptibility of the tumour xenografts to the growth inhibitory effects of ketoconazole and CsA was determined. The tumour cell lines used in this study included a human colon carcinoma, HT-29, a human malignant melanoma, SKMEL, and a murine malignant melanoma, B16M. These tumour types were chosen because they represent common malignancies with high metastatic potential and high morbidity and mortality. In addition, relatively specific monoclonal antibodies (MoAbs) are available for all of these cell lines (DiMaggio et al, 1990). The experiment was designed to evaluate the growth inhibitory effects of CsA and ketoconazole, used alone or in combination, on the HT-29, SKMEL and B16M tumour cell lines in vitro.

GENERAL
Tumour Cell Line

Tumour cell lines HT-29, SKMEL and B16M were obtained from the American Type Culture Collection (ATCC, Rockville, Md., USA) and maintained in RPMI-1640 medium, (Flow Laboratories, Australian Biosearch, Karrinyup, Australia), containing 10% foetal calf serum (FCS, Cytosystems, Sydney, Australia), 2 mM L-glutamine, 100 mM sodium pyruvate, 100 mM non-essential amino acids, (all from Aust. Biosearch), and benzylpenicillin (100,000 units/l, Commonwealth Serum Laboratories (CSL), Parkville, Australia). All tumour cell lines were incubated at 37° C./5%$CO_2$/95% humidity and the medium was changed every 3 to 4 days. For passage and assay, cells were detached with 0.1% w/v trypsin/0.02% w/v versene (CSL).

MTT Assay 3-(4,5-dimethylthiazo-2-YL)-2,5-diphenyl-tetrazolium bromide (MTT) was obtained from Sigma Corporation (St. Louis, Mo, USA). The assay was performed according to the method of Mosmann (1983). In general, following incubation of the tumour cells with the CsA and/or ketoconazole (see below), the plates were centrifuged (1000 g, 5 min) and 100 μl of the supernatant removed. 20 μl of MTT (stock at 5 mg/ml in PBS) was added to each well and the plates incubated at 37° C. for 4 hours. 100 ul of 0.04N HCl-isopropanol was then added to each well and the dark blue formazan-crystals were dissolved by mixing. Optical densities (ODs) were determined at 590 nm using a Titertek multiscan photometer (Flow Labs.) and were directly proportional to cell growth (Mosmann, 1983).

In Vitro Assessment of Tumour Cell Growth

Tumour cells were seeded at 5 to $10 \times 10^3$/well (100 μl/well), incubated overnight at 37° C., and exposed to CsA or ketoconazole (0–60 μg/ml) for 1–3 days (final volume, 200 μl). Tumour cell growth inhibition was assessed using the MTT assay.

Results

The results are presented as the estimated dose of each reagent required to reduce tumour cell growth by 50% (ie the $ED_{50}$) as determined from the linear portion of the growth inhibition curve, and are shown in FIG. 6 and Table 4.

TABLE 4

$ED_{50}$ of CsA and Ketoconazole on B16M, HT-29 and SKMEL in vitro.[a]

| Test Reagent | Tumor Cell Line | | |
|---|---|---|---|
| I CsA | B16M | HT-29 | SKMEL |
| days in culture: | $ED_{50}$ (μg/ml) | | |
| day 1 | 28.8 ± 3.8 | 29.6 ± 3.6 | 31.5 ± 2.1 |
| day 2 | 18.5 ± 1.0 | 23.3 ± 2.9 | 30.0 ± 1.2 |
| day 3 | 10.2 ± 3.3 | 15.3 ± 3.2 | 25.5 ± 4.1 |
| EtOH/Cremophor/saline vehicle: | vehicle conc. (%/ml) | | |
| day 3-$ED_{50}$ | (0.035%) | (0.053%) | (0.08%) |
| II Ketoconazole | B16M | HT-29 | SKMEL |
| days in culture: | $ED_{50}$ (μg/ml) | | |
| day 1 | 22.8 ± 2.8 | 23.8 ± 2.5 | 31.0 ± 2.6 |
| day 2 | 21.2 ± 4.3 | 18.2 ± 1.8 | 30.0 ± 1.1 |
| day 3 | 18.2 ± 3.9 | 12.7 ± 2.0 | 28.3 ± 1.7 |
| EtOH/Methanol vehicle: | vehicle conc. (%/ml) | | |
| day 3-$ED_{50}$ | (0.06%) | (0.035%) | (0.85%) |

[a]The effects of CsA and ketoconazole on tumour cell growth in vitro were determined using the MTT assay. The data are presented as the $ED_{50}$ (± SD) in μg/ml for each tumour cell line following exposure for 1, 2, or 3 days in culture. The vehicle concentration present in the day 3 $ED_{50}$ sample is indicated in the parentheses as %/ml. Each tumour cell line was tested 3–5 times.

$ED_{50}$ Determination of CsA and Ketoconazole

All three tumour cell lines tested were found to be moderately to highly resistant to the growth inhibitory effects of CsA and ketoconazole, demonstrating $ED_{50}$s at or well above the maximum therapeutic plasma concentration for both reagents, ie. 0.10 μg/ml (Borel, 1989; Reynolds et al, 1992; Eichenberger et al, 1989a; FIG. 6, Table 4). The murine melanoma cell line, B16M, was found to be the most susceptible of the three tumour cell lines to CsA, demonstrating an $ED_{50}$ of 10.2±3.3 μg/ml compared to 15.3±3.2 μg/ml and 25.5±4.1 μg/ml for the human HT-29 and SKMEL tumour cell lines, respectively. Conversely, ketoconazole was found to be most inhibitory to HT-29 tumour cell growth, demonstrating an $ED_{50}$ of 12.7±2.0 μg/ml compared to 18.2±3.9 μg/ml and 28.3+1.7 μg/ml for B16M and SKMEL, respectively (FIG. 6, Table 4). Neither the CsA vehicle (Cremaphor EL/EtOH/saline) nor the ketoconazole vehicle (EtOH/methanol) inhibited tumour cell growth at concentrations present in the $ED_{50}$ doses of CsA or ketoconazole for the 3 tumour cell lines. Slight inhibition (10–15%) of B16M and HT-29 cell growth was observed following 3 days exposure to the Cremphor/EtOH/Saline vehicle at concentrations of 0.1%, and this inhibition has been corrected for in all experiments.

Isobologram Analysis of Interaction Potential of CsA and Ketoconazole

The interaction potential of the combination of CsA and ketoconazole on tumour cell growth in vivo was determined by isobologram analysis (Czarniecki et al, 1984). The $ED_{50}$s of CsA (0–60 μg/ml) in combination with 3 sub-optimal ketoconazole concentrations (determined from the ketoconazole $ED_{50}$ for each line), and ketoconazole (0–60 μl/ml) in combination with 3 sub-optimal CsA concentrations, were determined and plotted as a fractional inhibitory concentration (FIC) of the $ED_{50}$ of CsA, or of ketoconazole alone, which has a designated FIC of 1. Based on this comparison, if the FIC values of the CsA/ketoconazole combination form a convex curve, the interaction potential is considered antagonistic. If the values fall in a straight line the effects are additive, and if the points form a concave curve, the effects are synergistic. Confirmation of the synergistic, additive or antagonistic nature of the CsA/ketoconazole interaction was determined using the additivity model (Welander et al, 1985). The fractional survival of the individual reagents is determined and the two values are multiplied together. The product of the two values becomes the expected cell survival, and is compared with the observed fractional survival when the two reagents are tested together. A synergistic response is defined by an observed fractional survival which is 0.5 of the expected survival, an additive response by an observed fractional survival of 0.5 to 1.5 times the expected survival, and an antagonistic or subadditive response by an observed survival which is 1.5 the expected survival.

The isobologram analysis suggested that the growth inhibitory effects of CsA and ketoconazole, when used in combination, were additive to subadditive on the B16M and HT-29 tumour cell lines and additive to synergistic on the SKMEL tumour cell line, as shown in FIG. 7. Analysis of the data using the additivity model demonstrated that the growth inhibitory effects of the combination CsA/ketoconazole were additive on all three tumour cell lines, as shown in Table 5. Some CsA/ketoconazole combinations did approach synergism (ie. observed/expected fractional survival of <0.5), but in all cases, one or both of the reagents was present at a concentration ≧10 μg/ml (ie greater than the maximum therapeutic dose in humans). These results are summarised in Table 5.

TABLE 5

Interaction Potential of CsA and Ketoconazole on B16M, HT-29 and SKMEL[1]

| CSA + Keto (μg/ml) | | Exp. (OD) B16M | Obs. | Obs/Exp. | CSA + Keto (μg/ml) | | Exp. (OD) HT-29 | Obs. | Obs/Exp. | CSA + Keto. (μg/ml) | | Exp. (OD) SKMEL | Obs. | Obs/Exp. |
|---|---|---|---|---|---|---|---|---|---|---|---|---|---|---|
| 1.0 | 3.75 | 0.727 | 0.731 | 1.01 | 2.5 | 3.0 | 0.680 | 0.671 | 0.99 | 5.0 | 6.25 | 0.688 | 0.682 | 0.9 |
|  | 7.5 | 0.699 | 0.701 | 1.00 |  | 6.0 | 0.563 | 0.539 | 0.96 |  | 12.5 | 0.558 | 0.594 | 1.06 |
|  | 11.25 | 0.670 | 0.720 | 1.07 |  | 9.0 | 0.235 | 0.320 | 1.36 |  | 18.75 | 0.546 | 0.620 | 1.13 |
| 2.5 | 3.75 | 0.826 | 0.820 | 0.99 | 5.0 | 3.0 | 0.550 | 0.517 | 0.94 | 10.0 | 6.25 | 0.688 | 0.604 | 0.88 |
|  | 7.5 | 0.766 | 0.736 | 0.96 |  | 6.0 | 0.456 | 0.444 | 0.97 |  | 12.5 | 0.558 | 0.512 | 0.92 |
|  | 11.25 | 0.699 | 0.636 | 0.91 |  | 9.0 | 0.190 | 0.188 | 0.99 |  | 18.75 | 0.546 | 0.559 | 1.02 |
| 5.0 | 3.75 | 0.740 | 0.715 | 0.97 | 10.0 | 3.0 | 0.300 | 0.212 | 0.71 | 20.0 | 6.25 | 0.564 | 0.513 | 0.97 |
|  | 7.5 | 0.687 | 0.648 | 0.94 |  | 6.0 | 0.248 | 0.142 | 0.57 |  | 12.5 | 0.428 | 0.447 | 1.00 |
|  | 11.25 | 0.661 | 0.658 | 1.00 |  | 9.0 | 0.104 | 0.054 | 0.52 |  | 18.75 | 0.422 | 0.386 | 0.91 |
| 2.5 | 1.5 | 0.735 | 0.798 | 1.09 | 2.5 | 3.75 | 0.679 | 0.603 | 0.89 | 5.0 | 3.75 | 0.640 | 0.734 | 1.15 |
|  | 3.75 | 0.702 | 0.880 | 1.25 |  | 7.5 | 0.559 | 0.623 | 1.11 |  | 7.5 | 0.577 | 0.628 | 1.09 |
|  | 7.5 | 0.511 | 0.583 | 1.14 |  | 11.25 | 0.353 | 0.352 | 1.00 |  | 11.25 | 0.491 | 0.453 | 0.92 |
| 5.0 | 1.5 | 0.724 | 0.789 | 1.09 | 5.0 | 3.75 | 0.632 | 0.519 | 0.82 | 10.0 | 3.75 | 0.627 | 0.602 | 0.96 |
|  | 3.75 | 0.696 | 0.798 | 1.05 |  | 7.5 | 0.520 | 0.499 | 0.95 |  | 7.5 | 0.559 | 0.596 | 1.07 |
|  | 7.5 | 0.504 | 0.544 | 1.08 |  | 11.25 | 0.328 | 0.233 | 0.71 |  | 11.25 | 0.473 | 0.342 | 0.72 |
| 10.0 | 1.5 | 0.785 | 0.750 | 0.96 | 10.0 | 3.75 | 0.427 | 0.377 | 0.88 | 20.0 | 3.75 | 0.582 | 0.518 | 0.89 |
|  | 3.75 | 0.759 | 0.751 | 0.99 |  | 7.5 | 0.351 | 0.265 | 0.76 |  | 7.5 | 0.525 | 0.4 | 0.82 |
|  | 7.5 | 0.547 | 0.419 | 0.77 |  | 11.25 | 0.221 | 0.119 | 0.54 |  | 11.25 | 0.447 | 0.283 | 0.63 |

[1]Interaction potentials of CSA/ketoconazole were determined using the additivity model. Combination CSA/ketoconazole experiments were performed 3 times on each cell line.

SUMMARY

These findings suggest that the anti-tumour activities of CsA and ketoconazole, alone and in combination, on the HT-29, SKMEL and B16M tumour cell line are minimal at doses which can be achieved in vivo. Thus the regimen of CsA and ketoconazole used to induce immunosuppression in the sheep model should not interfere with the establishment of human/murine tumour xenografts in situ which will serve as targets for the assessment of radiolabelled MoAb imaging and therapy.

Example 4

Transplantation of Cell Lines into Sheep

Tumour Cell Lines

The following human tumour cell lines are grown in the Cell Biology Research Unit at Fremantle Hospital.

| | | |
|---|---|---|
| 1. | LS174T (ATCC) | Colon carcinoma |
| 2. | HT 29 (ATCC) | Colon carcinoma |
| 3. | OVCAR-N1H3 (ATCC) | Ovarian carcinoma |
| 4. | CRL 1803 TT (ATCC) | Medullary cell carcinoma thyroid |
| 5. | SK MEL (ATCC) | Melanoma |
| 6. | HTB 3477 (Oncogen) | Breast |
| 7. | JAM | Serous cystadeno carcinoma of ovary |
| 8. | Control B16M | Murine melanoma |

Cells were maintained in media recommended by the American Type Culture Collection (ATCC). Specifically, the cell lines were maintained in 75 cm² tissue culture flasks (Costar, USA) in RPMI 1640 (Life Technologies, USA) supplemented with 10% fetal calf serum (FCS) and 100U/ml penicillin (CSL, Australia) and for NIH:OVCAR-3, 10% extra FCS and human insulin NIH:OVCAR-3 adenocarcinoma of ovary (Actrapid, Novo Nordisk, Denmark) at 10 $\mu$g/ml were added to the media. Confluent cells were harvested using trypsin-versene (CSL, Australia) and counted, then washed twice with PBS to remove FCS and resuspended at a concentration of $10^8$ cells/ml immediately prior to injection into sheep. All tumour cell lines were incubated at 37° C./5% $CO_2$/95% humidity and the medium was changed every 3–4 days. For passage and assay, cells were detached with 0.1% w/v trypsin/0.02% w/v versene.

For some experiments, tumours were passaged in nude mice and then transplanted into the immunosuppressed sheep as small solid tumour pieces approximately 2 mm×2 mm diameter.

Following acclimatization, weighing and shearing of the sheep, a jugular venous catheter was inserted subcutaneously under local anaesthetic, exiting the skin at the back of the neck.

Twice daily intravenous administration of 3 mg/kg cyclosporin was given via the indwelling jugular vein catheter each day for up to 70 days. A drench oral administration of ketoconazole was also given on a daily basis according to standard Murdoch University veterinary techniques in sheep. Parenteral administration of CsA in sheep and concomitant oral ketoconazole had minimal side effects in a controlled environment.

Haematological, biochemical and CsA assays were performed on a weekly basis on blood obtained directly from the jugular vein.

Reagents

CsA in powder form was dissolved in alcohol and Cremaphor EL according to the protocol developed at Fremantle Hospital.

Solutions were prepared on a weekly basis and diluted with physiological saline as required for daily aliquots to provide a dose of CsA determined by trough level assay. The typical daily dose of CsA was 6 mg/kg given in an indwelling jugular vein catheter in 2 divided doses given in the morning and evening.

The cyclosporin may be administered by a continuous infusion pump into the jugular vein to acheive greater control of serum Cs levels and minimize expensive drug use.

Ketoconazole powder was prepared in a drench formulation as follows:

36 g of ketoconazole was gradually added to about 400 ml of solution containing the following:

| | | |
|---|---|---|
| 1. | Ultrasil | 6.96 g, |
| 2. | Citric Acid | 2.78 g, |
| 3. | Sodium Citrate | 5.92 g, |
| 4. | Keltrol | 1.46 g, |
| 5. | PEG 6000 | 20.9 g, |
| 6. | MYRJ | 15.3 g, |
| 7. | Potassium Sorbate | 1.05 g, | and to which 0.78 ml of concentrated 10M HCl and 0.84 ml of 40% formalin had been added.

The resulting mixture was stirred for 30 minutes after which 200 ml of warm tap water was added. The mixture was again left to stir for at least one hour, after which the volume was made up to a final total of 720 ml. After mixing well, the solution was aliquoted and stored at 4° C. The final concentration of ketoconazole in this solution was 50 mg/ml and the dose given to the sheep may be 10 mg/kg or 1 ml of the solution per 5 kg sheep weight. Prior to giving the ketoconazole to sheep, the solution should be well mixed to distribute any sedimented powder although care should be taken to avoid frothing or aeration of the solution.

The basic ingredients of the drench were derived from the standard preparation used for oral administration of medication to ruminants at the School of Veterinary Studies at Murdoch University. The drench formulation of ketoconazole ensures abomasal delivery and effectively bypasses the rumen following oral administration to the sheep, and thus rendering the ketoconazole readily bioavailable.

The daily oral dose of ketoconazole was 20 mg/kg in 2 divided doses, given in the morning and evening.

CsA and Ketoconazole Assays

CsA assays were performed at the Western Australian Centre for Pathology and Medical Research using the EMIT® Cyclosporin Assays (Syva Co, San Jose, Calif., USA) on blood taken immediately before the morning dose. These trough CsA levels were maintained in the optimum range for immunosuppression between 750 and 1500 ng/ml.

Trough blood level assays performed at the Western Australia Centre for Pathological and Medical Research showed that ketoconazole plasma concentration was in the range 2.5–3.5 mg/L.

Immunological Assessments a) Mitogen Responses

Peripheral blood lymphocytes were tested on a weekly basis for capacity to respond to a series of mitogens. Lymphocytes were obtained from heparinized blood drawn from the anterior brachial vein by centrifugation and separation on a Ficoll/hypaque gradient. After washing, lymphocytes were dispensed into microliter trays at $5 \times 10^6$ cells/ml with an equal volume (100 $\mu$l) of RPMI containing phytohaemagglutinin, concanavalin A or pokeweed mitogen at 5, 10, and 20 $\mu$g/ml, together with 2-mercapto-ethanol, foetal calf serum and penicillin/streptomycin. Cells were cultured in an atmosphere of 5% $CO_2$ for 72 hours and were pulsed with ³H-thymidine at 0.5 $\mu$Ci/well over the final 16 hours of culture. After harvesting, radioactivity of cells was counted in the scintillation counter and stimulation indices determined:

$$SI = \frac{cpm \text{ mitogen stimulated cells} - cpm \text{ background}}{cpm \text{ nonstimulated cells} - cpm \text{ background}}$$

The functional capacity of lymphocytes was determined weekly.

b) Lymphocyte Phenotyping

To identify perturbations in number and proportion of B and T cells during chronic CsA induced immunosuppression, the phenotype of lymphocytes, prepared as above, was determined by immunofluorescence assay using a range of commercially available ovine monoclonal reagents. After labelling, suspensions were assayed by fluorescence-activated cell sorting. These assays provide an assessment of fluctuations in total B and T lymphocyte populations as well as T cell subjects. The results were expressed as percentages of total lymphocyte numbers.

c) Monitoring of Skin Allografts

Comparison of skin allografts with skin homografts on a daily basis constitutes an in vivo measure of cell-mediated immunity.

Skin and Tumour Transplantation Procedures

Five days after the initiation of CsA and ketoconazole administration, the animals were premedicated with rompun and subjected to general anaesthesia using halothane via an endotracheal tube.

Full thickness skin autograft and heterograft transplantations were performed on the flanks following standard procedures.

Cell Injections

Injections were given via a 21G needle as 0.1 to 0.3 ml cells in PBS with or without 0.1 ml Matrigel (Collaborative Biomedical Products, USA). For co-injection of cells with Matrigel all cells, syringes and needles were pre-chilled on ice, and the needle and syringe held in the injection site until the Matrigel had gelled.

A minimum of two human tumours was inoculated subcutaneously in each sheep under the bare skin of the inguinal region. At laparotomy, subcapsular and hepatic intraparenchymal inoculation of at least 2 tumour cell types was performed (one acting as the non-specific control for the labelled monoclonal antibody). Inoculation of the peritoneum under direct vision was also performed at the sites which were marked with a suture for ready identification at subsequent laparoscopies. Breast cancer cells were inoculated subcutaneously in the thorax and into chest wall and pleura to simulate common sites of local spread.

(i) Skin sites $10^7$ LS174T, SK-MEL, HT-29, OVCAR-3 and JAM cells in PBS were injected subcutaneously 5 cm apart on the shaved sides and flanks of the sheep at 4 injection sites for each cell line. Up to three different cell lines were injected into a individual sheep. For biodistribution studies 8 sheep received 4 subcutaneous injections each of LS174T; HT-29 and SK-MEL.

(ii) Intra-Abdominal Injections

The following procedures were carried out aseptically under halothane general anaesthetic in the animal operating room. At laparatomy the cells were injected with or without Matrigel using a 1 ml tuberculin syringe and a 21G needle. Non-absorbing sutures were placed 2 cm from injection sites for subsequent location at laparascopy or autopsy. The abdominal incision was closed in layers and the sheep monitored in the recovery room until post-operative recovery was complete.

(a) Ovarian and Peritoneal Wall Injections:

Three sheep received $2\times10^7$ JAM cells +0.1 ml Matrigel in the opposite ovary and two peritoneal wall sites. Before closure of the peritoneum OVCAR-3 cells were injected into the peritoneal cavity of one sheep.

(b) Colon, liver and peritoneal wall injection:

Four sheep received $10^7$ LS174T cells+0.1 ml Matrigel injected into 4 sites along the colon wall and 2 sites in the liver and peritoneal wall as well as one injection each in the liver and peritoneal wall of $10^7$ LS174T cells without Matrigel.

(iii) Solid Tumour Transplantation

Solid tumour pieces were harvested from nude mice and cut into 2 mm×2 mm cubes for transplantation into the sheep. Each transplantation site corresponded to the location of predilection for each tumour type in human metastasis.

Monitoring Tumour Growth

Skin tumours were measured weekly in two dimensions with calipers excised from the skin at varying times and fixed in formalin for subsequent histological examination. At autopsy 3–6 weeks after tumour cell inoculation appropriate organs and draining lymph nodes were removed and examined macroscopically and fixed in formalin for histology.

Tissues were also fixed in neutral buffered formalin and processed through alcohol and xylene to paraffin.

Sections were cut at $4\mu$ on a rotary microtome, dried at 60° C. and stained with Harris haematoxylin (H&E stain) and aqueous eosin on a random access staining machine. These were then coverslipped using a resin mounting medium and viewed under light microscopy.

Mucins in tissues were demonstrated using the periodic acid-Schiff reaction (P.A.S). Mucins were oxidised by periodate to expose aldehydes which were demonstrated with Schiffs reagent. Any glycogen in the tissue was removed by prior treatment with fresh malt diastase.

Antigen demonstration was achieved by a peroxidase conjugated streptavidin staining procedure. The primary antibody was first applied to the tissue sections which were then further labelled with a biotinglated link antibody followed by a streptavidin peroxidase enzyme conjugate. The bound peroxidase enzyme was then visualised with a diaminobenzidine substrate.

Tumour xenografts of Icc could be imaged with a gamma camera after administration of suitable gamma-emitting radionuclide labelling of tumour specific monoclonal antibodies.

In addition to documentation of tumour cell death and toxic radiation, effects on normal organs, excisional biopsy and histopathological examination were used for quality control of the model to ensure the absence of host reaction and rejection of the tumour xenografts.

Throughout each study, animals were observed for pain and distress by monitoring food and water intake and observing changes in general well-being and presence of teeth grinding. No post-procedural pain was anticipated. If changes to these parameters occurred, the animals were euthanased by intravenous lethabarb. Otherwise, animals were euthanased within 70 days of tumour implantation.

Animals were imaged under halothane general anaesthesia when subcutaneous tumours reached a size of at least 1.0 cm. Gamma imaging was performed at intervals appropriate to the physical half-life of the radionuclide used to label the monoclonal antibody.

Results

Immunesuppression of Sheep with CsA and Ketoconazole

When the Merino-Dorset lambs used were immunosuppressed, aseptic conditions were not required and no sterilization of food and water was necessary (in contrast to the sterile environment required for maintenance of nude mice and rats).

The weight remained relatively constant over the period of immunosuppression, as the anorexic effect of CsA was balanced by the anticipated natural weight gain of 3 kg per week.

Sheep Skin Autografts and Heterografts

Full thickness sheep skin heterografts were transplanted into CsA/ketoconazole immunosuppressed sheep, and compared with full thickness skin autograft transplants. Given maintenance of trough plasma CsA levels in the optimum range, the skin heterograft appearance was identical to that of the adjacent autografts, both macroscopically and microscopically. However, if the CsA was stopped or fell below a critical level, rejection processes occurred and the graft became non-viable within 10 days.

Mouse Tumour Xenografts

Implantation of B16 tumour pieces and inoculation of suspension of $10^7$ cells at each subcutaneous site gave rise to viable tumours which regularly attained a diameter of greater than 1 cm at 3 weeks. Inoculations of $10^7$ cells into peritoneum and subserosally in colon, under direct vision at laparotomy, also generated viable B16 melanotic murine tumour nodules at these intra-abdominal sites in the sheep.

Human Tumour Xenografts

The human tumours successfully transplanted into the immunosuppressed sheep included the human colon carcinoma cell lines HT-29 and LS 174T, which elaborate CEA, and a human amelanotic melanoma, SKMEL and OVCAR-3 and JAM results are represented in FIGS. 14 and 15.

Subcutaneous inoculations of $10^7$ cells at each site gave rise to viable tumours of 1.5–2 cm diameter within 3 weeks at almost all sites for each human tumour type. Histological examination demonstrated abundant mitoses in xenografted tumour cells, with no significant necrosis and absence of host inflammatory cell reaction. The morphology of the tumours was true to type in that the less well-differentiated HT29 colon cancer manifested few glandular structures, and peroxidase staining demonstrated less elaboration of CEA than the well-differentiated LS174T tumour, in which abundant CEA activity was observed, particularly on the luminal surfaces of the glandular formations. Similarly, mucin production reflected the degree of differentiation of these tumour cells, and was much more prominent in LS174T xenografts.

Xenografts of SMEL remained amelanotic, and showed abundant S100 staining typical of human melanomata.

Tumour cell spheroids of LS174T cells were also prepared. The spheroids which were 300 mm in diameter and comprised $8 \times 10^3$ LS174T cells, were administered via the portal vein under direct vision at laparotomy, in an attempt to simulate intrahepatic metastases of human colon carcinoma in the sheep liver. Similarly, pulmonary metastases were simulated by the intravenous administration of LS174T spheroids.

Orthotopic transplantation of LS174T human colon cancer in our sheep was achieved by inoculation of $10^7$ cells into the wall of stomach and colon and hepatic matastases were induced by intravenous administration by portal vein or simulated by intrahepatic inoculation, and direct subperitoneal implantation was also successful. Spontaneous metastasis to liver or lymph nodes was not observed in these animals possibly due to the relatively short duration of the experiment (3 weeks). Studies of metastasis may be facilitated by orthotopic implantation of intact human tumours (Fu et al, 1991) which would be relatively easy in the sheep in comparison with mice and may be performed at multiple sites in the same animal.

For example, human colon tumour pieces or inoculation of cells may be orthotopically implanted submucosally in the distal colon under sigmoidoscopic control without requirement for abdominal surgery. Such sigmoid tumours may then be monitored endoscopically, and serial biopsies taken as required. We have used a similar endoscopic approach to orthotopically transplant human bladder carcinoma cells in Matrigel beneath the vesical urothelium in sheep via an operating paediatric cystoscope. Matrigel, a reconstituted basement membrane matrix preparation (Fridman et al, 1991), was found to facilitate tumour graft acceptance at sites of cell inoculation, particularly for OVCAR NIH3 and JAM human ovarian carcinoma cells orthotopically transplanted into sheep ovaries. Enhancement of tumour growth was also observed following transplantation of multicell spheroids of LS174T cells in comparison with inoculation of LS174T single cell suspenstion at the same sites. We also found that LS174T xenografts grown subcutaneously in nude mice from cell inoculations, when implanted into the immunesuppressed sheep subdermally or explanted on the wall of colon as tumour chunks, the xenografts grew more rapidly than xenografts arising from inoculation of LS174T single cell suspensions. The uptake of $^{131}$I-A5B7 anti-CEA monoclonal antibody was similar for such implanted tumour pieces to that observed in subcutaneous LS174T xenografts originating from inoculation of cell suspensions, and both were demonstrated on gamma camera images taken 3–5 days following administration of the radiolabelled anti-CEA antibody.

Example 5

Localization and Imaging of Human Tumour Xenografts Using Radiolabelled MoAb.

Intravenous administration of $^{131}$I-radiolabelled anti-CEA MoAb, A5B7 (Celltech Ltd, Slough UK), to CsA/ketoconazole immunosuppressed sheep bearing subcutaneous xenografts of human HT29, LS174T colon carcinoma and SKMEL human melanoma allowed gamma camera imaging of 1–2 cm of colon cancer xenografts at 3 and 5 days after injection of the radiopharmaceutical. The nonspecific control SKMEL tumours were not detected. The tumour localization of CEA-specific $^{131}$I MoAb was confirmed by gamma counting, which showed the greatest accumulation of radioactivity within LS174T xenografts, a lesser amount in HT29 cells and only background activity in the nonspecific SKMEL melanoma xenograft.

The uptake of $^{131}$I-A5B7 in LS174T human colon cancer xenografts in the immunosuppressed sheep ranged between 0.014 and 0.035% DI/g, higher activities being observed in hepatic sites as shown in Table 6. This tumour uptake is in accord with that achieved in human colonic tumours studies in patients using $^{131}$I-A5B7 anti-CEA-monoclonal antibody, where peak uptake of 0.018% DI/g was observed at 27 hours after administration of radiolabelled intact antbody (Lane et al, 1994). These modest tumour uptakes in sheep contrast with those achieved in LS174T human colon cancer xenografts in nude mice where $^{131}$I-A5B7 peak tumour uptake is over 20% DI/g (Pedley et al, 1993). These relatively high human tumour uptakes of radiolabelled antibodies are commonly achieved in nude mouse xenografts (Siler et al, 1993; Senekowitsch et al, 1989) but the typical uptakes for the same antibody and tumour type in man, are around 0.005% DI/g (Dykes et al, 1989; Begent et al, 1990). Expectations of curability of tumours by radioimmunotherapy, based on nude mouse model results are therefore unrealistic. For example, if a 60 Gy dose in one week is considered sufficient for tumour sterilization and given a tumour uptake of $^{131}$I-labelled monoclonal antibody of 0.005% DI/g the corresponding whole body radiation absorbed dose would be 17 Gy (Vaughan et al, 1986). The maximum tolerable whole body dose in man is in fact around 2 Gy, and new approaches to radioimmunotherapy of solid tumours will be necessary. One such approach is regional therapy, and the comparable size and anatomy of the sheep will facilitate exploration of methods of local and intra-tumoral radioimmunotherapy. For example, we have inoculated our immunosuppressed sheep with human tumour cells in liver, peritoneum and bladder to prvide models for regional radioimmunotherapy delivered via hepatic artery, or intra-peritoneal and intra-vesical injection. Monitoring by quantitative gamma camera imaging is easily performed in this large animal model and results can be correlated with counting of biopsy samples and autoradiography to validate algorithms for calculation of dosimetry in patients in subsequent clinical trials to evaluate safety and efficacy of radioimmunotherapy of cancer.

cardiac inoculation of tumour cells, providing a model of bone marrow metastases in breast cancer patients.

The animal model of the invention will also be useful in the developmental and/or evaluation of novel ligands to permit targetting of therapeutic agents to the tumours. This may be achieved, for example, by radiolabelling of antibodies raised against these ligands (eg. "tumour specific" monoclonal antibodies) with therapeutic radionuclides such as Rhenium-188, Holmium-166 and Samerium-153 without compromising immunoreactivity and without in vivo breakdown of the labelled antibody.

We have used a similar endoscopic approach to orthotopically transplant human bladder carcinoma cells in Matrigel beneath the vesical urothelium in sheep via an operating paediatric cystoscope.

TABLE 6

HUMAN TUMOUR XENOGRAFTS IN IMMUNE-SUPPRESSED SHEEP
$^{131}$I-A5B7 anti-CEA IgG1 Mab
% DI/gm: mean (Sd)

|  | 1 DAY (n = 1) | 3 DAYS (n = 2) | 5 DAYS (n = 5) | 7 DAYS (n = 5) |
|---|---|---|---|---|
| BLOOD | 0.0279 (0.0039) | 0.0263 (0.0008) | 0.0142 (0.0059) | 0.0124 (0.0028) |
| LIVER | 0.0091 (0.0014) | 0.0066 (0.0001) | 0.0051 (0.0032) | 0.0040 (0.0018) |
| SPLEEN |  | 0.0027 (0.0007) | 0.0036 (0.0011) | 0.0034 (0.0012) |
| B.M |  | 0.0035 (0.0008) | 0.0038 (0.0013) | 0.0027 |
| KIDNEY |  | 0.0059 (0.0008) | 0.0054 (0.0018) | 0.0050 (0.0014) |
| HEART |  |  | 0.0054 (0.0001) | 0.0025 (0.0000) |
| LUNG |  |  | 0.0115 (0.0022) | 0.0064 (0.0009) |
| SK MEL S/C |  | 0.0040 (0.0011) | 0.0027 (0.0014) | 0.0040 (0.0020) |
| HT 29 S/C |  | 0.0068 (0.0008) | 0.0085 (0.0065) | 0.0053 (0.0011) |
| LS 174T S/C | 0.0291 (0.0025) | 0.0126 (0.0049) | 0.0130 (0.0050) | 0.0102 (0.0049) |
| LS 174T STOMACH | 0.0207 |  | 0.0266 |  |
| LS 174T COLON |  |  |  | 0.0051 (0.0005) |
| LS 174T PERITONEUM | 0.0188 |  | 0.0208 (0.0052) |  |
| LS 174T LIVER |  |  | 0.0342 (0.0068) | 0.0111 (0.0036) |

The SKMEL tumours showed typical morphological charcterisitcs of human melanoma and did not accumlate any of the radiolabelled anti-CEA antibody taken up by the colonic xenografts. Only the melanoma was observed to metastasize from subcutaneous sites of inoculation and SKMEL cells were subsequently recovered from the regional pre-stifle lymph node, grown in cell culture and reinoculated subcutaneoulsy in sheep and gave rise to tumours morphologically indistinguishable from those of the primary inouclation. The failure of colon cancer to metastasize from subcutaneous sites of inoculation has been observed consistently in nude mice (Fidler, 1990; Kubota, 1994) and orthotopic transplantation has been advocated to maintain the malignant phenotype of human tumour xenografts (Radinsky and Fidler, 1992). For melanoma, the subcutaneous route of cell inoculation represents orthotopic transplantation and regional lymph node metastases were demonstrated in our sheep.

SUMMARY

The results of these experiments demonstrate that we have established a large animal model of immunosuppression in the sheep which allows successful transplantation of skin grafts and tumour xenografts. Tumour cell transplantation in this model can be performed at various sites (subcutaneous, intra-abdominal, intrahepatic, intrapulmonary and intracardiac) to simulate primary and metastatic tumour localization. Transplantation of tumour spheroids can also be performed.

The animal model of the invention will enable us to produce bone marrow metastases of breast cancer by intra- Lastly, we have clearly demonstrated the ability to perform specific radioimmuno-scintigraphy of human tumour xenografts in sheep, and this model will aid preclinical evaluation of the efficacy of potential radioimmunotherapy for a variety of human metastatic cancers.

Bladder carcinoma cells BL-17/0/X1; J82; 5637 in Matrigel are injected into the urothelium of 6–10 sheep via a cystoscope. The sheep are monitored by cystoscopy and small biopsies taken to confirm tumour growth and phenotype.

After an appropriate time, for example 5 weeks, the sheep with visible tumours are injected intravesically with Samarium-153 labelled C1–137, 595 or cytokeratin-8 or labelled isotype control antibody, or with labelled EGF or unlabelled EGF as control. Subsequent cystoscopy is performed 5 and 10 days later to monitor tumour growth. Tumour and surrounding urothelium are examined histologically at autopsy.

Yttrium-90 labelled octreotide (Novartis) is a somatostatin analogue which targets somatostatin receptors on carcinoid, small cell lung cancer or the like. This enables radiopeptide receptor therapy to be studied, using an animal model of the invention, and which has been inoculated in the liver with human carcinoid BON cells in Matrigel.

Treatment of glioma by administration of Yttrium-90 octreotide may also be studied in sheep which have been subjected to orthotransplantation by injection of glioma cells directly into the frontal lobe of the brain.

The animal model described herein may also be used for direct transplantation of tumours, including human tumours freshly taken from surgical specimens. This has the advantage of preserving the malignant phenotype of the tumour, and the propensity to metastasize when transplanted orthotopically. The expression of specific tumour associated antigens, which can be lost during passage in cell culture, can also be preserved.

The unique attribute of the large animal model of human tumours, in contrast to the mouse, is the ability to measure uptake of radioactivity in tumours and critical normal organs, by quantitative SPECT imaging in vivo and to verify the time course of accumulation of tumour radioactivity by serial biopsies for gamma counting. When MoAbs are radiolabelled with isotopes such as Iodine-131, Holmium-166, Samarium-153, Rhenium-186, Rhenium-188, Copper-64, Scandium-47 and Lutetium-177, which emit both beta and gamma rays, dosimetry of radiotherapeutic activities may be measured in vivo and cancericidal effects verified by serial tumour biopsy and histological and microautoradiographic correlation.

In addition to documentation of tumour cell death and toxic radiation effects on normal organs, excisional biopsy and histopathological examination are used for quality control of the model to ensure the absence of host reaction and rejection of the tumour xenografts.

Other Uses of the Animal Model for Studying Cancer

Radioimmunoscintigraphy of metastatic breast carcinoma has been disappointing (Kahn et al, 1993), but recent clinical testing of a new, commercially available monoclonal antibody BrE-3 which is reactive against a mucin epitope has shown encouraging localization, and therapeutic potential has been postulated (Kramer et al, 1993). The animal model of the present invention is useful to test this hypothesis.

"Humanized" S193, a murine monoclonal antibody raised against Lewis Y antigen of breast carcinoma, has little cross-reactivity with blood epitopes, and the developmental work currently in progress at the Ludwig Institute in New York may result in the availability of $^{131}$I-labelled humanised S193 Mab. We are exploring the possibility of testing this new radioimmunotherapeutic agent in our large animal model.

Recent reports of enhancement of radioimmunotherapeutic effects on xenografts of human breast cancer in nude mice by using concomitant external beam irradiation (Warhoe et al, 1992), and reports of synergistic effects of interferon gamma (Buchsbaum et al, 1991) may also be investigated in our large animal model.

In addition to the modelling of human cancer metastases, the CsA immunesuppressed sheep, having organs of comparable size to those of the human, allows direct organ implantation of human tumour cells to create xenografts which simulate primary malignancy. For example, cells from human glioma may be relatively easily inoculated into the brain of the immunosuppressed sheep to facilitate the study of efficacy of various primary treatments such as targeted chemotherapy, radiopharmaceutical therapy, or local internal or external radiation treatments.

Likewise, myeloma cells can be inoculated directly into the marrow of the long bones or spleen in this large animal model.

The model of the invention may also be used to study the effects of gene therapy or the control of metastasis by a gene of interest. For example, cancer suppressor genes such as the p53 gene, the DCC (deleted in colon carcinoma) gene, the metastasis regulating gene, nm23, or any tumour-suppressor or inhibitor gene of interest which can be inserted into a vector such as a viral vector or liposome, may be co-implanted or inoculated with cells as described above.

Alternatively, genetically manipulated cells containing these genes may be transplanted into the animal model. The genes may also be introduced after xenografting and metastasis at the site of the tumour formation. The effects of gene therapy alone, or in combination with the forms of therapy already described, can then be investigated.

Whether the goal of treatment is to sterilize primary or secondary human tumours, the CsA-immune-suppressed sheep model provides an in vivo system of comparable size and physiology to human patients and allows detailed study of targeted cancer therapy.

In the particular instance of radioimmunotherapy, the size of the organs permits tumours which mimic neoplasms in patients presenting with early cancer to be studied under controlled conditions, particularly by organ imaging modalities such as gamma camera SPECT, CT or MRI which are impractical in nude mice or rats.

In addition to accurate measurement of pharmacokinetics of potential therapeutic agents, the tumour specificity and localization in the human cancer cells can be measured directly, and the time relationships examined by serial excisional biopsy and histochemical or quantitative microautogradiographic examination, or gamma or beta scintillation counting.

Safe therapeutic application of novel tumour specific radiolabelled monoclonal antibodies requires preclinical delineation of critical organ dosimetry such as can be measured by SPECT imaging of a large animal human tumour model, validated by serial biopsies of major organs for accurate gamma or beta counting. The target tumour dosimetry can also be accurately measured by well counting of excisional biopsies to establish the potential efficacy of any radiopharmaceutical prior to embarking upon a clinical trial. Computer algorithms can then be developed, and tested, to perform prospective critical organ dosimetry on tracer doses of radioimmunotherapeutic agents, validated by direct measurement in the large animal model as described above, to accurately prescribe a maximum safe tolerated dose to a patient before committing to therapy.

It will be apparent to the person skilled in the art that although the examples have been described in some detail for the purposes of clarity and understanding, they represent guidelines only. The person skilled in the art will recognise that various modifications and alterations to the embodiments and methods described herein may be made without departing from the scope of the inventive concept disclosed in this specification.

References listed herein are identified on the following pages, and are incorporated herein by this reference.

REFERENCES

Barbera-Guillem E, Canavate M L, Lopez de Tejada I and Vidal-Vanaclocha F (1988) Influence of Host Defenses on the Hepatic Colonization of B16F1O Melanoma Cells. Clin Expt Metastasis 6(2):153–169.

Begent R H J, Pedley R B (1990) Antibody targeted therapy in cancer: Comparison of Murine and clinical studies: Cancer Treatment Reviews 17:373–378.

Bodey G P (1992) Azole Antifungal Agents. Clin Infect Dis. 14(suppl 1):s161–169.

Borel J F (1989) Pharmacology of Cyclosporin (Sandimmune). IV Pharmacological Properties in vivo. Pharmacol Rev 41(3):259–372.

Borelli D, Bran J L, Fuentes J, Legendre R, Leiderman E, Levine H B, Restrepo A and Stevens D A (1979) Ketoconazole, an Oral Anti-fungal: Laboratory and Clinical Assessment of Imidazole Drugs. Postgrad Med J 55(647):657–661.

Bowers V D et al (1991) The Haemodynamic Effects of Cremophor EL. Transplantation 51(4):847–850.

Breckenridge A (1992) Clinical Significance of Interactions with Antifungal Agents. Br J Dermatol. 126(suppl 39):19–22.

Butman S M, Wild J C, Noland P E, Fagan T C, Finley P R, Hicks M J, Mackie, M J and Copeland J G (1991) Prospective Study of the Safety and Financial Benefit of Ketonazole as Adjunctive Therapy to Cyclosporin after Heart Transplantation 10(3):351–358.

Buchsbaum D J (1991) Experimental Radioimmunotherapy: Methods to Increase Therapeutic Efficacy Relevant to the Study of Human Cancer. Antibody Immunoconjugates and Radiopharmaceuticals 4(4):693–701.

Charles B G, Fillipich L J and Pass M A (1993) Pharmacokinetics and Absolute Bioavailability of Cyclosporin Following Intravenous and Abomasal Administration to Sheep. J. Pharm Pharmacol 45:821–824.

Charles B G et al (in press 1995) Pharmacokinetics and Absolute Bioavailability of Cyclosporin Following Intravenous and Abomasal Administration to Sheep. J Pharm Pharmacol.

Czarniecki C W, Fennie C W, Powers D B and Estell D A (1984) Synergistic Anti-viral and Antiproliferative Activities of *Escherichia coli*-derived Human Alpha, Beta and Gamma Interferons. J. Virol. 49:490–496.

de Waard-Siebinga I, van Delft J L, de Wolff-Rouendaal D and Jager M (1994) Hamster Greene Melanoma in the Rabbit Eye: Immunosuppressive Treatment to Improve this Tumour Model. Graefe's Arch Clin Exp Opthalmol 232:683–688.

DiMaggio T J, Scheinberg D A and Houghton A N (1990) Monoclonal Antibody Therapy of Cancer. In: Cancer Chemotherapy and Biological Response Modifiers (Eds. H M Pinedo, D L Longo and B A Chabner) vol 11, chap 12, pp 177–203, Amsterdam, Elsevier Sci Publ.

Di Padova FE (1989) Pharmacology of Cyclosporine (Sandimmune) V. Pharmacological Effects on Immune Function: in vitro studies. Pharmacol Rev. 41(3):373–405.

Dusci L J, Hackett L P, Chiswell G M and Ilett K F (1992). Comparison of Cyclosporin Measurement in Whole Blood by High Performance Liquid Chromatography, Monoclonal Fluoroscene Polarization Immunoassay, and Monoclonal Enzyme Multiplied Immunoassay. Therap Drug Monit 14:327–332.

Dykes P W, Bradwell A R, Chapman C E, Vaughan A T M (1987) Radioimmunotherapy of cancer: Clinical studies and limiting factors: Cancer Treatment Reviews 14:87–106.

Eichenberger T, Trachtenberg J, Toor P and Keating A (1989a) Ketoconazole: A Possible Direct Cytotoxic Effect on Prostate Carcinoma Cells. J of Urology 141:190–191.

Eichenberger T, Trachtenberg J, Chronis P and Keating A (1989b) Synergistic Effect of Ketoconazole and Antineoplastic Agents on Hormone-Independent Prostatic Cancer Cells. Clin & Invest Med 12(6):363–366.

Fidler I. (1990) Critical factors in the biology of human cancer metastasis: Twenty-eighth G.H.A. Clowes Memorial Award Lecture. Cancer Research 50:6130–8.

First M R, Schroeder T J, Alexander J W, Stephens G W, Weiskittel P, Myre S A and Pesce A J (1991) Cyclosporin Dose Reduction by Ketonazole Administration in Renal Transplant Patients. Transplant. 51(2) 365–370.

First M R, Schroeder T J, Micahel A, Hariharan S, Weiskittel P, Alexander J W (1993). Cyclosporine-Ketoconazole Interaction. Long-term Follow-Up and Preliminary Results of a Randomised Trial. Transplantation 55:1000–1004.

Fridman R, Kebbey Mc, Royce L S, Tomas M Z, Sweeney M, Jicha D L et al (1991). Enhanced tumour growth of both primary and established human and murine tumour cells in athymic mice after coinjection with Matrigel. Journal of National Cancer Institute 83:11;769–74.

Fu X, Besterman J M, Monosov A, Hoffman R M (1991). Models of hu,man netastatic colnon cancer in nude mice orthotopically constructed by using histologically intact patient specimens. Proc Natl Acad Sci 88:9345–9349.

Gomez D Y, Wacher V J, Tomlanovich S J, Herbert M F, Benet L Z (1995). The Effects of Ketoconazole on the Intestinal Metabolism and Bioavailability of Cyclosporin. Clin Pharmac Ther 58:15–19.

Gupta Sk, Legg B, Soloman L R, Johnson R W G and Rowland M (1987) Pharmacokinetics of Cyclosporin: Influence of Rate of Constant Intravenous Infusion in Renal Transplant Patients. Br. J. Clin. Pharmac. 24:519–526.

Hess A D, Esa A H and Colombani P M (1988) Mechanisms of Action of Cyclosporin: Effect on Cells of the Immune System and on Subcellular Events in T Cell Activation. Transplant. Proc 29(2) suppl 2:29–40.

Hu L K, Huh K, Gragondas E S and Yowy L H Y (1994) Establishment of Pigmented Choroidal Model Retina 14(3):264–269.

Kahn D, Weiner G J, Huston B M, Dowlatshahi K, Feole J, Kaplan E H, Grossman J, Joyce J M and Acierno J B (1993) The Pharmacokinetic and Diagnostic Accuracy of Low-dose Indium 111-labelled B72.3 (CYT-103) in Patients with Metastatic Breast Cancer. Antibody, Immunoconjugates and Radiopharmaceuticals 6(2) 141–153.

Keogh A, Spratt P, McCosker C, Macdonald P, Kaan A. (1995) Ketoconazole to Reduce the Need for Cyclosporin After Cardiac Transplantation. New England Journal of Medicine 333:628–633

Kramer E L, deNardo S J, Liebes L, Kroger L A, Noz M E, Mizrachi H, Salako Q A, Furmanski P, Glenn S D, deNardo G L and Ceriani R. (1993) Radioimmunolocalization of Metastatic Breast Carcinoma Using Indium-111 Methyl Benzyl DTPA BrE-3 Monoclonal Antibody: Phase I Study. Journal of Nuclear Medicine 34(7):1067–1074.

Kreis W and Soricelli A (1979) Cyclosporins: Immunosuppressive Agents with Anti-tumour Activity. Experientia 35:1506–1508.

Kubota T. (1994) Metastatic models of human cancer xenografted in the nude mouse: The importance of orthotopic transplantation. Journal of Cellular Biochemistry 56:4–8.

Lane D M, Eagle K F, Begent R H J, Hope-Stone L D, Green A J, Casey J L et al (1994). Radioimmunotherapy of metastatic colorectal tumours with iodine-131-labelled antibody to carcinoembryonic antigen: Phase 1/II study with comparative biodistribution of intact and F9ab')$_2$ antibodies. Br J Cancer 70:521–5.

Liggett P E, Lo G, Pince K J, Rao Na, Pascal S G and Kan-Mitchel J (1993) Heterotransplantation of Human Uveal Melanoma. Grafe's Arch Clin Exp Opthalmol 231:15–20.

Mahler C and Denis L (1992) Management of Relapsing Disease in Prostate Cancer. Cancer 70(suppl 1):329–334.

Manzotti C, Audisio R A and Pratesi G (1993) Importance of Orthotopic Implantation for Human Tumours as Model Systems: Relevance to metastasis and Invasion. Clin. Exp. Metastasis 11:5–14

Mosmann T (1983) Rapid Colorimetric Assay for Cellular Growth and Survival: Application to Proliferation and Cytotoxicity Assays. J Immunol. Meth. 65:55–63.

Patton P R, Brunson M E, Pfaff W W, Howard R J, Peterson J C, Ramos E L, Karlix J L (1994). A Preliminary Report of Diltiazem and Ketoconazole. Their Cyclosporin-Sparing Effect and Impact on Transplant Outcome. Transplantation 57:889–892.

Pedley R B, Boden J A, Boden R, Dale R, Begent R H J. (1993) Comparative radioimmunotherapy using intact of F9ab')$_2$ fragments of $^{131}$I anti-CEA antibody in a colonic xenograft model. Br J Cancer 68:69–73.

Radinsky R, Fidler I. (1992) Regulation of tumour cell growth at organ-specific metastases. In vivo 6:325–332.

Reynolds D J M and Aronson J K (1992) Cyclosporin. Br. Med. J 305:1491–1494.

Russ G R (1992) Complications of Immunosuppressive Therapy in Transplantation. 2 Specific Immunosuppressive Agents. Med. J Aust. 157(4):264–267.

Senekowitsch R, Reidel G, Mollenstadt S, Kriegal H, Pabst H W. (1989) Curative radioimmunotherapy of human mammary carcinoma xenografts with Iodine 131-labelled monoclonal antibodies. J Nucl Med 30:531–537.

Siler K, Eggensperger D, Hand P H, Milenic D E, Miller L S, Houchens D P et al (1993). Therapeutic efficacy of a high-affinity anticarcinoembryonic antigen monoclonal antibody (COL-1_. Biotechnology Therapeutics 4:163–181.

Tresham J J, Whitworth J A, de Lima J J G, McDougall J G and Scoggins B A (1988) Dihydrocyclosporin D in Sheep: Haemodynamic and Renal Effects. Clinical and Experimental Pharmacology and Physiology 15:419–425.

Vaughan A T M, Bradwell A R, Dykes P W, Anderson P. (1986) Illusions of tumour killing using radiolabelled antibodies. The Lancet 1492–1493.

Wadhwa N K, Schroeder T J, Pesce A J, Myre S, Clardy C W and First M R (1987) Cyclosporin Drug Interactions: A Review. Ther. Drug Monit. 9(4):399–406.

Warhoe K A, deNardo S J, Wolkov H B, Doggett E C, Kroger L A, Lamborn K R and deNardo G L (1992) Evidence of External Beam Irradiation Enhancement of Radiolabeled Monoclonal Antibody Uptake in Breast Cancer. Antibody Immunoconjugates and Radiopharmaceuticals 5(2):227–235.

Welander C E, Morgan T M, Homesley H D, Trotta P P and Spiegel R J (1985) Combined Recombinant Human Interferon Alpha 2 and Cytotoxic Agents Studied in a Clonogenic Assay. Int. J. Cancer 35(6):721–729.

Wiseman G A, Applebaum F R, Eary J F, Beaumier P L, Kunz L L and Nelp W B (1991) Multiple Xenografts of Human Malignant Melanoma in the Dog—A Model for Radiolabelled Monoclonal Antibody Targeting. J Nucl Med 32:1056.

What is claimed is:

1. A method of evaluating the efficacy of an agent used to treat or image cancer, comprising administering said agent to an animal model of cancer, said model comprising a ruminant mammal which has been immunosuppressed by intravenous administration of cyclosporin together with oral ketoconazole, fluconazole, or calcium channel blocker and wherein the animal carries a tumor xenograft.

2. The method of claim 1, wherein said cyclosporin is CsA, CsB, CsC, CsD, CsE, CsF, CsG, CsH, and CsI, or a derivative, analogue or homologue thereof.

3. The method of claim 1, wherein said mammal has a plurality of xenografted tumors.

4. The method of claim 1, wherein the tumor is of human origin.

5. The method of claim 1, wherein the tumor is of non-human origin.

6. The method of claim 1, wherein the xenografted tumor is obtained by transplantation of tumor into said mammal, said tumor being selected from the group consisting of a fresh surgical specimen, a tumor cell line, a cell from a solid tumor, a spheroid of cancerous cells, and a tumor piece obtained from a tumor passaged in a host animal.

7. The method of claim 1, wherein the tumor xenograft is selected from the group consisting of bladder cancer, ovarian cancer, bowel cancer, colon cancer, lung cancer, breast cancer, brain cancer and melanoma.

8. The method of claim 1, wherein the agent is a potential therapeutic agent.

9. The method of claim 6, wherein the potential therapeutic agent is a cytokine, a chemotherapeutic agent, a radiopharmaceutical, an internal radioactive agent, an external radioactive agent or a radiolabeled peptide.

10. The method of claim 8, wherein the therapeutic agent is a gene therapy agent.

11. The method of claim 1, wherein the agent is a radioimaging agent.

* * * * *